United States Patent
Li

(10) Patent No.: US 7,795,014 B2
(45) Date of Patent: *Sep. 14, 2010

(54) DISPOSABLE REACTOR MODULE AND DETECTION SYSTEM

(75) Inventor: Dongqing Li, Waterloo, CA (US)

(73) Assignee: InstantLabs Medical Diagnostics Corp., Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/535,526

(22) Filed: Aug. 4, 2009

(65) Prior Publication Data

US 2010/0041050 A1 Feb. 18, 2010

Related U.S. Application Data

(63) Continuation of application No. 11/543,004, filed on Oct. 4, 2006, now Pat. No. 7,569,382.

(60) Provisional application No. 60/723,644, filed on Oct. 5, 2005.

(51) Int. Cl.
C12M 1/22 (2006.01)
B01J 19/00 (2006.01)

(52) U.S. Cl. .................... 435/305.1; 422/130
(58) Field of Classification Search ............ 435/305.1
See application file for complete search history.

(56) References Cited

U.S. PATENT DOCUMENTS

| 5,674,742 | A | 10/1997 | Northrup et al. | |
|---|---|---|---|---|
| 6,432,364 | B1 | 8/2002 | Negami et al. | |
| 6,529,277 | B1 | 3/2003 | Weitekamp | |
| 6,706,519 | B1 | 3/2004 | Kellogg et al. | |
| 6,762,049 | B2 * | 7/2004 | Zou et al. | 435/287.2 |
| 7,130,061 | B2 | 10/2006 | Singh et al. | |
| 7,297,313 | B1 * | 11/2007 | Northrup et al. | 422/131 |
| 7,342,663 | B2 | 3/2008 | Matsushita et al. | |
| 7,364,897 | B2 * | 4/2008 | Heaney et al. | 435/287.2 |
| 7,569,382 | B2 * | 8/2009 | Li | 435/305.1 |
| 2003/0087282 | A1 | 5/2003 | Oshida et al. | |
| 2003/0219754 | A1 * | 11/2003 | Oleksy et al. | 435/6 |
| 2004/0029258 | A1 | 2/2004 | Heaney et al. | |
| 2004/0232550 | A1 | 11/2004 | Walker et al. | |
| 2004/0241691 | A1 | 12/2004 | Bachi | |
| 2004/0262550 | A1 | 12/2004 | Singh et al. | |
| 2005/0106612 | A1 | 5/2005 | Amirkhanian et al. | |

FOREIGN PATENT DOCUMENTS

WO WO/2005/054826 6/2005

OTHER PUBLICATIONS

Bassler et al., "Use of a Fluorogenic Probe in a PCR-Based Assay for the Detection of Listeria monocytogenes," Applied and Environmental Microbiology 61:10, 3724-3728 (1995).

Belder et al., "Surface modification in microchip electrophoresis," Electrophoresis 24, 3595-3606 (2003).

(Continued)

Primary Examiner—Walter D Griffin
Assistant Examiner—Lydia Edwards
(74) Attorney, Agent, or Firm—Fish & Richardson P.C.

(57) ABSTRACT

A disposable reactor module, monitoring/optical detection system and related hardware for, inter alia, chemical reactions including Polymerase Chain Reactions.

18 Claims, 12 Drawing Sheets

OTHER PUBLICATIONS

Belgrader et al., "A Battery-Powered Notebook Thermal Cycler for Rapid Multiplex Real-Time PCR Analysis," Analytical Chemistry 73: 2, 286-289 (2001).
Giordano et al., "Polymerase Chain Reaction in Polymeric Microchips: DNA Amplification in Less Than 240 Seconds," Analytical Biochemistry, 291, 124-132 (2001).
Lin et al., "Simulation and experimental validation of micro polymerase chain reaction chips," Sensors and Actuators B 7, 127-133 (2000).
Munro et al., Analytical Chemistry, 73:8, 1784-1794 (2001).
Nagai et al., "Development of a Microchamber Array for Picoliter PCR," Analytical Chemistry 73:5, 1043-1047 (2001).
Witham et al., "A PCR-Based Assay for the Detection of *Escherichia coli* Shiga-Like Toxin Genes in Ground Beef," Applied and Environmental Microbiology, 62: 4, 1347-1353 (1996).
Yang et al., "High sensitivity PCR assay in plastic micro reactors," The Royal Society of Chemistry Lab Chip, 179-187 (2002).
Office Action dated Jun. 24, 2008 issued in U.S. Appl. No. 11/543,004.
Response to Non-Final Office Action issued in U.S. Appl. No. 11/543,004, filed Sep. 24, 2008.
Office Action dated Jan. 28, 2009 issued in U.S. Appl. No. 11/543,004.
Response to Final Office Action issued in U.S. Appl. No. 11/543,004, filed Apr. 24, 2009.
U.S. Appl. No. 60/723,644, filed Oct. 5, 2005, Disposable Reactor Module and Detection System.
Notification of Transmittal of the International Search Report and Written Opinion, International Application No. PCT/US06/39053, Jul. 11, 2008, 13 pages.

* cited by examiner

1—PCR marker   2 – E.ColiO157:H7 DNA (amplified on chip system)
3&4 – BAC (DJ0416J11) DNA (amplified on chip system)
5 – Genomic DNA(2054) at chip coated with 1%PVP (amplified on chip system)
6 – Genomic DNA (2054) at chip without coating (amplified on chip system)
7&8 – BAC(DJ0416J11) DNA amplified on PCR machine Fig. 17 Comparative results of PCR tests with different DNAs using the chip system and a commercial PCR machine.

1 -- PCR marker
2,3,4,5&6-- Genomic DNA (2054) amplified on PCR chip system
7 & 8 -- Genomic DNA(2054) amplified on commercial PCR machine Fig. 18 Results of PCR tests with genomic DNA (2054) under different conditions with the chip system

SEQUENCE LISTING

<160> NUMBER OF SEQ ID NOS: 3

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
gactgcaaag acgtatgtag attcg                                         25

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
atctatccct ctgacatcaa ctgc                                          24

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
tgaatgtcat tcgctctgca ataggtactc                                    30

DISPOSABLE REACTOR MODULE AND DETECTION SYSTEM

CROSS-REFERENCE TO RELATED APPLICATIONS

This application is a continuation of U.S. application Ser. No. 11/543,004, filed on Oct. 4, 2006 which claims priority to U.S. application Ser. No. 60/723,644, filed on Oct. 5, 2005. The contents of each of these applications are incorporated herein by reference in their entirety.

BACKGROUND OF THE INVENTION

Technical Field

The present invention relates to the field of devices for performing chemical and/or biochemical reactions under a temperature-controlled environment. More particularly, the present invention relates to a device for real-time monitoring/detecting of Polymerase Chain Reaction.

Analytical processes that only require small amounts of DNA have many applications in various fields, such as microbiology, forensics, food science, bio-defense, and water purification. Another application of such processes is for pre-implantation genetic diagnosis (PGD) where there is only one cell to work with and to extract DNA from. PGD requires an answer quickly so that the embryos can be selected to transfer back without having to freeze them.

Polymerase chain reaction (PCR) is a very valuable technique, because the reaction is highly specific, and capable of creating large amounts of copied DNA fragments from minute amounts of samples, for both sequencing and genotyping applications. For this reason, PCR has wide applications in clinical medicine, genetic disease diagnostics, forensic science, and evolutionary biology. Recently, miniaturized PCR devices have attracted great interest because they have many advantages over conventional PCR devices, such as portability, higher thermal cycling speed, and significantly reduced reagents/sample consumption. Most mini/micro PCR devices can be classified into two types, static chamber PCR chips and dynamic flow PCR chips.

The first type of device uses stationary thermal cyclers to heat and cool a static volume of liquid in a micro-chamber. In these devices, either the micro-chamber is manufactured separately and placed in contact with an external heater, or the micro-chamber and the micro-heater are bonded together to form a complete microchip. A portable PCR device has been described with specially designed ceramic heaters and the corresponding PCR tubes by Belgrader et al. [P. Belgrader et al., Analytical Chemistry, 73, 286 (2001)]. In their work, the PCR reaction was achieved in a very short time period but the total reaction volume was still as large as conventional PCR. The micro PCR system designed by Yang et al. [J. Yang et al., Lab on a Chip, 2, 179 (2002)] controlled the temperature of a micro PCR reactor by two Peltier thermoelectric devices sandwiching the reactor. Because heat sinks and fans are attached to the Peltier thermoelectric devices for better thermal management, it is difficult to operate the PCR and access the PCR chip after the installation. Lin et al [Y. C. Lin et al., Sensors and Actuators B: Chemical, 71, 127 (2000)] use a PCR system with a reaction well fabricated in a silicon wafer sealed with a glass substrate and place a heater at the bottom of the silicon wafer. In this design, a small reaction volume is used to improve the temperature uniformity. However, it is difficult to fill and collect the PCR solution through the two holes on the top cover. Nagai et al. [H. Nagai et al., Analytical Chemistry, 73, 1043 (2001)] pattern micro-chambers of varying sizes onto silicon wafers and run the PCR using a commercial thermal cycler. PCR chips with a reaction chamber and a micro-heater patterned onto a silicon wafer using micro-fabrication technologies are also widely used in other PCR works to speed up the heating and cooling processes during the PCR cycles. Because of the integrated micro-heater and temperature sensor, all chips are fabricated using photolithography, metal film deposition, etching, and oxidation processes, etc. Thus, they are very expensive unless the chips are fabricated in high volume production. Giordano et al. [B. C. Giordani et al., Analytical Biochemistry, 291, 124-132 (2001)] focuses an infrared light onto a polyimide chip and heats a small volume of PCR sample very quickly. However, the infrared heating system is complicated and increases the operation cost greatly.

The second type of device, a dynamic flow-through PCR device, heats and cools PCR reactants by flowing the reactants through different temperature zones. A typical flow-through thermal cycler is one with thin film platinum heaters and sensors patterned onto a silicon wafer to generate three different temperature zones. A flow-through thermal cycler using thermal convection flow also exists. Another flow-through PCR chip pumps the reagents between three reaction chambers using a bi-directional peristaltic pump. PCR reactions are also achieved in a continuous flow mode by pumping in a ring chamber with controlled temperature regions. Compared to the first type of PCR device, the flow-through type can reduce the heating and cooling time and thus shorten the total time of PCR reaction. However, it is difficult to examine the PCR results and to collect the PCR product in the second type of PCR system. Reliability of this type of device cannot be assured unless reliable pumping and inter-channel connection are available at an acceptable cost.

Research has also been done towards integrating PCR with either pre-PCR or post PCR processes to further utilize the advantages of microfluidics. Real-time PCR, as it is known, is highly attractive because it can detect and quantify PCR results through real-time analysis of fluorescent signals generated during the reaction, without the conventional post-PCR processes such as gel electrophoresis.

In real-time PCR [Bassler, H. A. et al. The use of a fluorogenic probe in a PCR-based assay for the detection of *Listeria monocytogenes*. Appl. Environ. Microbiol. 61 (1995) 3724-3728; Livak, K. J. et al. Oligonucleotides with fluorescent dyes at opposite ends provide a quenched probe system useful for detecting PCR product and nucleic acid hybridization. PCR Methods Appl. 4 (1995) 357.362], a reporter fluorescence dye and a quencher dye are attached to an oligonucleotide probe. Negligible fluorescence from the reporter dye's emission is observed once both dyes are attached to the probe. Once PCR amplification begins, DNA polymerase cleaves the probe, and the reporter dye is released from the probe. The reporter dye, which is separated from the quencher dye during every amplification cycle, generates a sequence-specific fluorescent signal. Real-time PCR detection is based on monitoring the fluorescent signal intensity produced proportionally during the amplification of a specific PCR product (e.g., an *E. coli* DNA); therefore, it is a direct and quantitative method with high sensitivity. Such a method has been used to detect *E. coli* Shiga-like toxin genes in ground beef [Witham P. A., Yamashiro, C. T., Livak, K. J. and Batt, C. A., A PCR based assay for the detection of *Escherichia coli* Shiga-like toxin genes in ground beef *Appl Environ Microbiol* 1996; 62:1347-1353].

Real-time technologies have been applied by using FAM dye conjugated probes (a fluorescence dye; there is 5-FAM, 6-FAM and 5/6-FAM, its full name is 5-carboxyfluorescein or 6-carboxyfluorescein) and SYBR green dyes. Through these processes, the real-time PCR reactions are conducted in customized flat polypropylene tubes with optical windows for fluorescence detection, the reaction volume ranging from 25 µL to 100 µL. The requirement of a large amount of DNA template limits these applications. There also exists a miniature spectrometer capable of detecting a spectrum of fluorescence by using DNA labeled SYBR green dye. However, this system uses a commercial capillary thermal cycler. The overall system does not differ very much from conventional real-time PCR systems.

While real-time PCR has significant advantages compared to regular PCR, there are limitations to the application of real-time PCR techniques. During real-time PCR, the optical detection system must monitor the fluorescence intensity in real time. At least two separate sets of excitation-detection wavelength pairs must be available at each PCR well to identify both the desired and control species in each well. As the number of wells and/or desired light interaction increases, the optical infrastructure grows greatly, increasing the complexity, cost, and size of the optical detection module.

Currently, the instruments for conducting real-time PCR are bulky and expensive, and are only available in a few large hospitals and major medical centers. Therefore, there is a need to develop an improved system that will allow this valuable technique to be more widely used.

SUMMARY OF THE INVENTION

In general, applications that involve detecting gene mutations, detecting bacteria and viruses, performing genetic testing, or the like, can be performed using the present invention. These applications can be found in the fields of microbiology, forensics, food science, water purification, etc. For the purpose of this description, the invention will be described specifically with respect to PCR, but should not be limited to that application. The present invention can be used with other various applications, such as Enzyme Linked Immuno Sorbent Assay (ELISA), which is a sensitive immunoassay that uses an enzyme linked to an antibody or antigen as a marker for the detection of a specific protein, especially an antigen or antibody. It is often used as a diagnostic test to determine exposure to a particular infectious agent, such as the AIDS virus, by identifying antibodies present in a blood sample.

The present invention provides a miniature device consisting of a reactor module made of a combination of glass and polymer and used with a miniature thermal cycler to perform real-time and regular PCR. Compared to silicon or glass PCR chips, the present device does not need micromachining or photolithography processes. The fabrication of the reactor modules of the invention is very simple and low in cost. These reactor modules are disposable after a single use. This can avoid the potential of contamination associated with other non-disposable PCR reactor modules due to reuse of the reaction chamber. In one embodiment, the present device fits a standard fluorescence microscope and thus it is possible to do real-time PCR tests using this system without an elaborate and expensive real-time PCR machine. This can make a real-time PCR test affordable to most biomedical laboratories by using their existing fluorescence microscopes. The present device is flexible in terms of the sample volume and the number of wells that can be changed according to the applications.

In addition, the present invention also provides a fluorescence detection system to establish a stand-alone real-time PCR system. The device may be made of a small enough size to be portable.

In accordance with a first broad aspect of the present invention, there is provided a disposable reactor module comprising: a non-reflective, thermally conductive substrate; and a layer of polymer on the substrate, the layer of polymer having at least one reaction well for receiving a fluid sample, the polymer being chemically inert, non-adherent to DNA, and reacting in a stable manner to heating and cooling.

In accordance with a second broad aspect of the present invention, there is provided a miniature multiplex fluorescence detection system for detecting fluorescence emissions from at least one sample on a reactor module having a plurality of reaction wells, the system comprising: at least one light source coupled to the reaction wells, for generating light at excitation wavelengths; at least one detector for receiving detection wavelengths from the reaction wells; and, an optical switching device, coupled between the detector and the reaction wells on the substrate, to direct emissions of fluorescence to the detector.

In accordance with a third broad aspect of the present invention, there is provided a method for real-time monitoring/detecting of a temperature-controlled chemical reaction involving fluorescence emissions, the method comprising: providing at least one fluid sample in a disposable reactor module comprising a non-reflective, thermally conductive substrate and a layer of polymer on the substrate, the layer of polymer having at least one reaction well for receiving the sample, the polymer being chemically inert, non-adherent to DNA, and reacting in a stable manner to heating and cooling; sealing at least one reaction well; heating and cooling the reactor module to allow the chemical reaction to progress in the at least one reaction well; directing excitation wavelengths to the sample to cause fluorescence emissions; capturing the fluorescence emissions from the sample; and monitoring the chemical reaction by processing the fluorescence emissions.

In accordance with a fourth broad aspect of the present invention, there is provided a system for real-time monitoring of a chemical reaction involving fluorescence emission-detection, the system comprising: a disposable reactor module, a sealant, a miniature multiplex fluorescence detection system for detecting fluorescence emissions from the samples on the reactor module having reaction wells, and a control module for controlling the fluorescence detection system and monitoring the chemical reaction by processing the fluorescence emissions. The reactor module comprises: a non-reflective, thermally conductive substrate; and a layer of polymer on said substrate, the layer of polymer having reaction wells for receiving fluid samples, the polymer being chemically inert, non-adherent to DNA, and reacting in a stable manner to heating and cooling. The sealant prevents evaporation of the fluid sample contained in the reaction wells of the reactor module. The fluorescence detection system comprises: at least one light source coupled to the reaction wells, for generating light at excitation wavelengths; at least one detector for receiving detection wavelengths from the reaction wells; and a fiber optical switching device, preferably corresponding to the number of reaction wells, coupled between the detector and the reaction wells on the substrate, to direct emissions of fluorescence to the detector. A heating and cooling module modulates the temperature of the samples, and a stage receives the reactor module and couples the reactor module to the heating and cooling module.

In one embodiment, the control module is connected to both the miniature reactor module and the fluorescence detection system. It controls and synchronizes the operation of the reactor module and the optical detection system. Alternatively, the fluorescence detection system is connected to a computer that will externally process the fluorescence emissions and monitor the chemical reaction.

In accordance with a fifth broad aspect of the invention, there is provided a device for real-time monitoring/detecting of a temperature-controlled chemical reaction involving fluorescence emission-detection, the device comprising: a miniature multiplex fluorescence detection system for detecting fluorescence emissions from samples contained in the reaction wells of a reactor module, the system comprising: at least one light source coupled to the reaction wells, for generating light at excitation wavelengths; at least one detector for receiving detection wavelengths from said reaction wells; an optical switching device, coupled between said detector and the reaction wells, to direct emissions of fluorescence to said detector; a heating and cooling module for modulating a temperature of said samples; a stage coupled to said heating and cooling module for receiving said reactor module; and, a control module for controlling the fluorescence detection system and monitoring the chemical reaction by processing the fluorescence emissions.

In one embodiment, the control module is connected to both the miniature reactor module and the fluorescence detection system. It controls and synchronizes the operation of the reactor module and the optical detection system. Alternatively, the fluorescence detection system is connected to a computer that will externally process the fluorescence emissions and monitor the chemical reaction.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENTS

The reactor module in accordance with one aspect of the present invention is used with a heating and cooling module. In one embodiment, the heating and cooling module is a miniature thermal cycler. In the examples described herein where fluorescence is being monitored, with the exception of the example described with reference to FIG. 15, this reactor module was placed on the stage of a standard fluorescence microscope, and the reaction was monitored using the fluorescence microscope.

Figure 1:
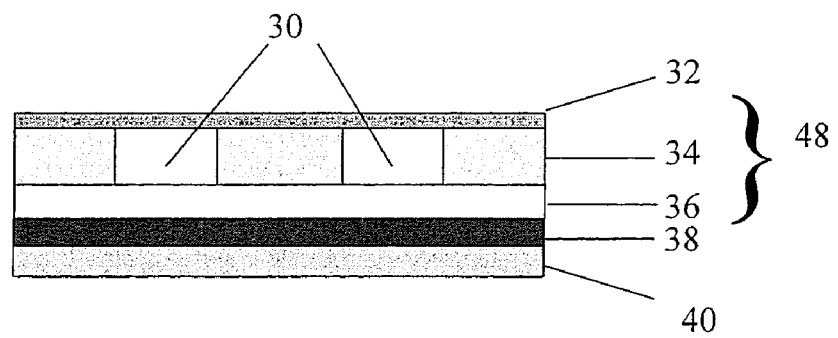
FIG. 1 is a cross-sectional view of the layer structure of the PCR chip.
Figure 2:
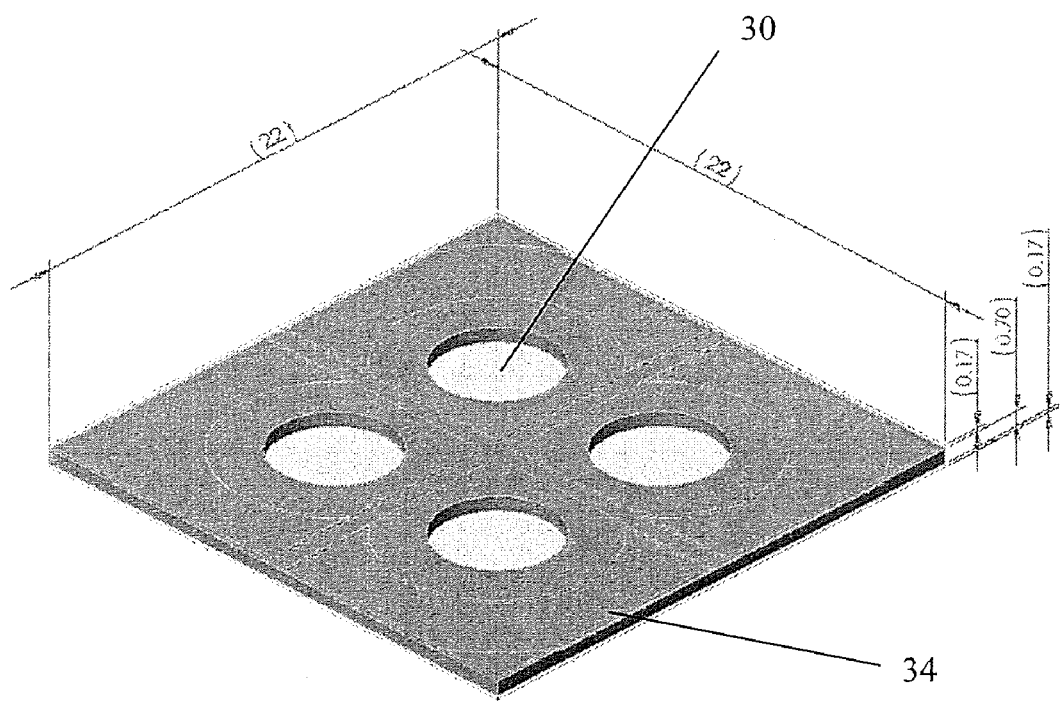
FIG. 2 is a top view of the PDMS layer of the reactor module with four reactant wells.

From hereon, the reactor module combined with the heating portion of the heating and cooling module will be referred to as a PCR chip. The PCR chip is illustrated in FIG. 1. Its overall dimension is shown in FIG. 2, which shows an example of a four-well chip. A single-well chip has the same overall dimensions, such as width, length and height. The only difference is the location of the well, as well as the structures around the well. The heater sits on a Teflon substrate 40, which can be fixed on the device chassis. PCR wells 30 are built in a PDMS layer 34, sit on the glass substrate 36, and are covered by a thin glass microscope cover slip 32 (0.1~0.2 mm). Then, these three layers, which in one embodiment of the invention form reactor module 48, sit on top of the heater 38. The heater 38 can be purchased from Omega (Model No. KHLV-101/10). The glass substrate 36 can be a commercial micro cover glass/cover slip(size: 22×22 mm).

While PDMS was chosen as the best material, other polymers such as PMMA (Polymethylmethacrylate) can be used. A person skilled in the art will readily identify that any material that is chemically inert, non-adherent to DNA, optically transparent, and reacts to heating and cooling in a stable manner can be used instead of PDMS. The advantage of using a cheap plastic like PDMS is that there is no micro-machining or lithographic process involved to make the wells, and therefore the overall costs of production are negligible. The reactor module itself becomes disposable and issues of contamination involved in cleaning and reusing this apparatus are no longer a problem.

Theoretically, a reactor module is a simple structure and can be made easily by constructing wells to contain PCR agents. However, there are great challenges in the design and fabrication of the reactor module when a miniature PCR chip is expected to be able to operate at a general condition, such as thirty cycles of denature (30 seconds), extension (30 seconds) and annealing (30 seconds) at each cycle. In one embodiment, the reactor module was fabricated using the PDMS casting, cutting and bonding techniques as described below.

The PDMS mold is manufactured using a soft lithography technique. Masters containing the desired chip pattern are made by spin coating SU-8 negative photoresist on a glass slide to a nominal thickness of 25 µm. The final thickness is decided by controlling the speed of the spinning coat machine. The relationship between the thickness and the speed can be further referred to in the data sheet for SU-8-25 photoresist provided by MicroChem Inc. The photoresist film is then hardened through a two stage direct contact pre-exposure bake procedure (65° C. for 5 min and 95° C. for 15 min) and exposed to UV light for 10 seconds through a transparency mask containing the desired chip pattern. A two-stage post-exposure bake procedure (65° C. for 1 min 95° C. for 2 min) is then used to enhance cross-linking in the exposed portion of the film. The slide is then placed in quiescent developer solution for 8 to 12 min to dissolve the unexposed photoresist, leaving a positive relief containing the chip pattern. Liquid PDMS is then poured over the master and cured at 65° C. for 6 to 12 h yielding a negative cast of the chip pattern (Generally, 10:1 PDMS and cure agency are used, but it was found 15:1 PDMS and cure agency give better results). In the cured PDMS with the chip pattern, through-holes are punched to form the reaction well when the PDMS layer is bonded with a glass plate. A thin layer of glass is used to cover the reactor module of the PCR chip after providing the reaction agents in the reaction wells and sealing the reaction well to keep the reaction agents from leaking out of the well.

Figure 3:
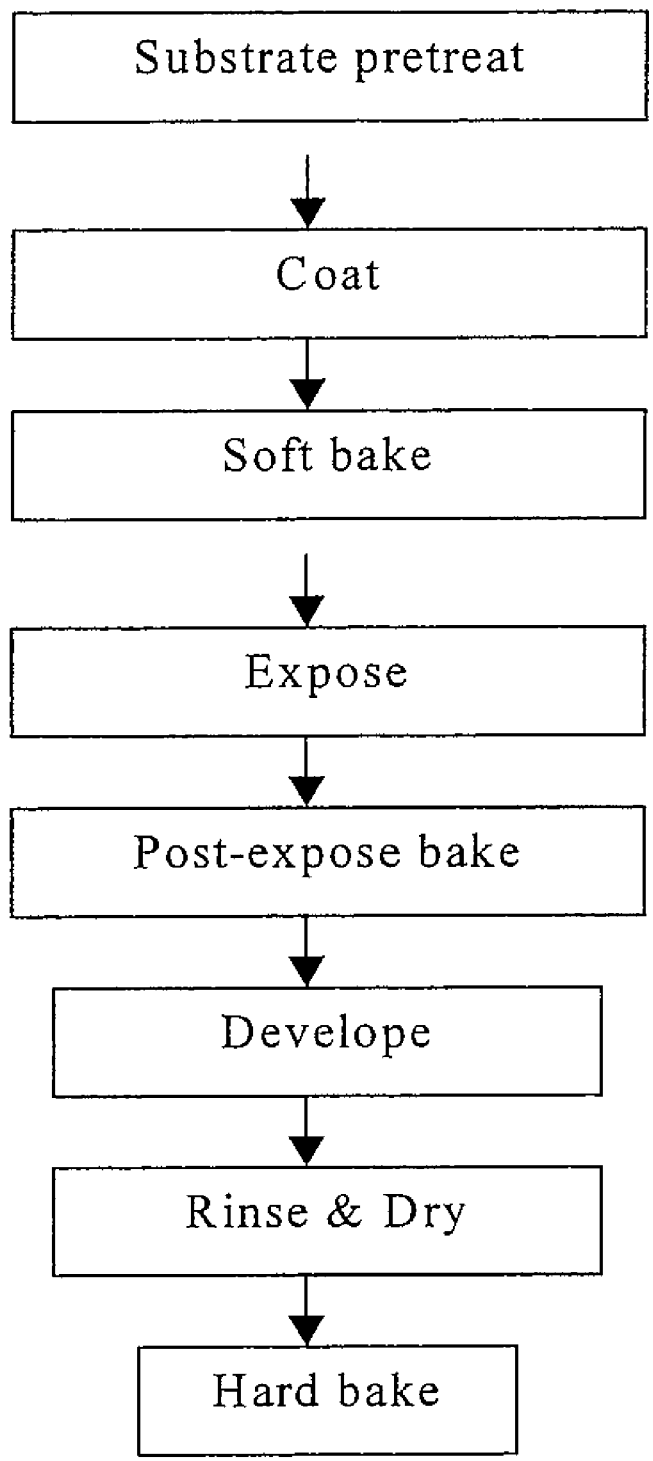
FIG. 3 is a flowchart of the fabrication of the casting molds.

The process for the master fabrication using SU-8 goes in steps as shown in FIG. 3, referring to the SU-8-25 datasheet provided by MicroChem. In the substrate pre-treat step, the glass substrate is soaked in acetone for half an hour (or the clean glass slides are stored in acetone before coating with SU-8 photoresist), is heated on the hot plate for half an hour and then is treated in the plasma cleaner for 2 minutes. The glass substrate is coated with SU-8-25 by using a spin coater, which is set to run at 500 rpm for 5 seconds and at 1200 rpm for 20 seconds.

Figure 4A:
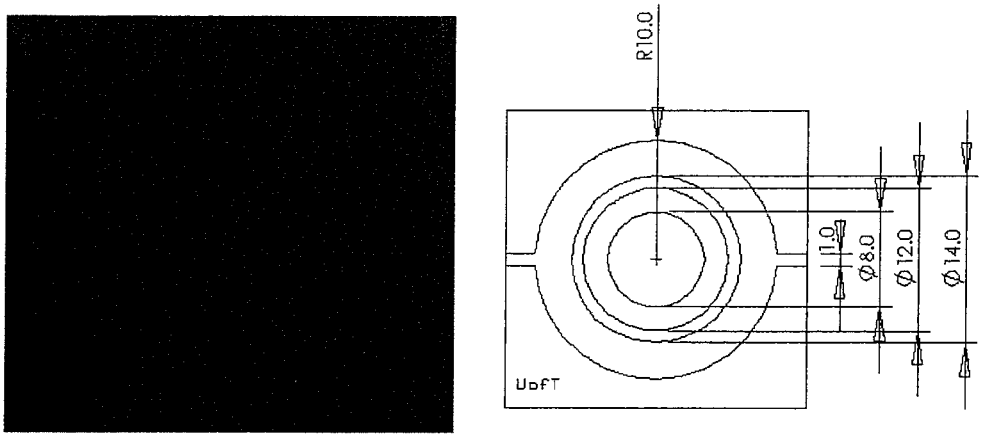
FIGS. 4A and 4B illustrate masks for the single-well and four-well PCR chips, respectively.
Figure 4B:
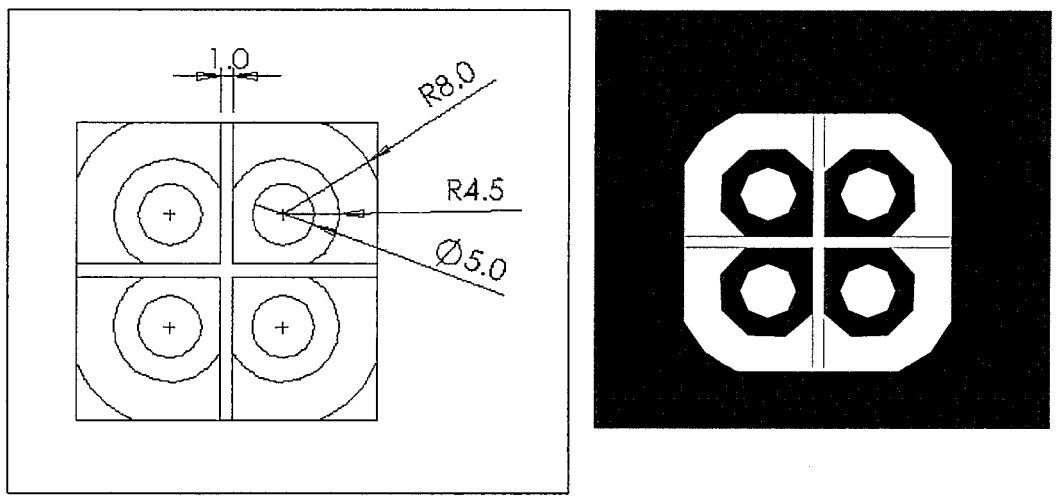

The two masks illustrated in FIGS. 4A and 4B are used to develop the PCR chips for single-well and four-well structures, respectively. These masks are used to create desired PDMS casting mold structures using the SU-8 negative photoresist. In FIGS. 4A and 4B, the white areas represent the transparent areas in the mask. This means that the white areas represent protrusive parts in the cast mold and the grooves in the reactor modules fabricated using the mold. Thus, in both the single-well structure (FIG. 4A) and the four-well structure (FIG. 4B), there are grooves around the reaction wells. These grooves around the reaction wells are used to enhance the sealing effect at the interface between the PDMS layer 34 and top cover glass 32. The grooves or spacers successfully break down the leakage links, provide a space for enfolding any bubbles which may form in the reaction well 30 during the heating process, and then avoid further spreading of the leaking gap. The dimension of the well 30 is decided based on the requirements of the amount of PCR reaction agent, as well as the overall size of the PCR chip. Preferably, the dimensions of the well provide for a volume of from about 0.1 µl to about 50 µl so that a sample of from about 0.1 µl to about 50 µl can be contained within the well. However, the volume of the well can be either larger or smaller to accommodate the given reaction.

A micro cover glass 32 deposited with a thin PDMS film is also fabricated for better bonding between the thin glass 32 and the PDMS layer 34. The coating process is conducted using the spin coat machine, which is set to operate at 500 rpm for 5 seconds and 3000 rpm for 20 seconds. This process results in a layer of PMDS film with thickness of around 20 to 30 µm. This thin PDMS layer not only improves the bonding results but also strengthens the thin glass and prevents it from breaking.

It was observed that the liquid in the wells 30 of the PCR chip dried out faster because of the bubbles generated in the wells when the chip is heated up. Some of them were dry within four or five cycles. This is a great challenge for the real PCR process because most of the PCR should run around 30 cycles to amplify the DNA to sufficient amounts. Liquid starts to leak out at the interfaces between the PDMS and glass cover. Since bubbles are generated at the high temperature, they push liquids out of the wells through any tiny gaps between the PDMS substrate and the glass cover. Therefore, a good seal of the PCR well is required to make the chip withstand the whole PCR process without being dried out. It was found that the structure w the grooves and/or the spacers about the wells of the present invention can withstand the thirty cycles at the required temperature profile for each cycle.

Figure 5:
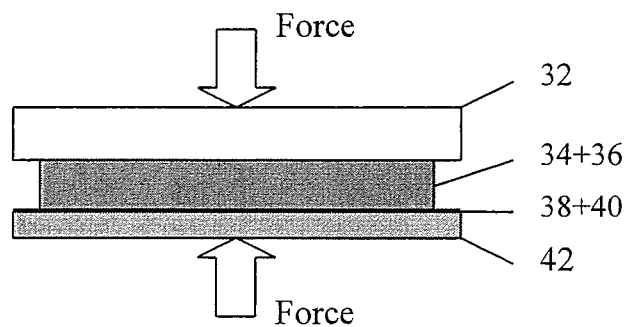
FIG. 5 is a schematic of the PCR chip installation with external forces.

In both of the single well structure and the four-well structure, grooves around the reaction well were used to enhance the sealing effect at the interface between the PDMS layer 34 and top glass cover 32. This cover breaks down the leakage links and then avoids further spreading of the leaking gap. The size of the grooves depend on the well size. The critical parameter is the thickness of the groove. The thicker the groove is, the better the sealing is. However, the thermal performance of the chip decreases if the thickness of the groove is too much. Ideally, the groove thickness should range from 40 micron to 500 micron. Although the self-sealing characteristics of the PDMS surface make it possible to seal the interface between the PDMS layer 34 and the PDMS-coated glass cover 32 to some extent, the different thermal expansion coefficients for the different materials, such as PDMS, glass, and reaction agents, result in different deformations in each material and thus the reaction agents may leak from the reaction wells. It is worse if bubbles are generated within the liquid when it is heated up. Therefore, to enhance the seal between the PDMS layer 34 and the glass cover 32, a mechanism, as shown in FIG. 5, was used to stop the leakage from the reaction wells by applying external forces. The PCR chip is placed on a support stage 42 and force is applied as shown to provide proper sealing. It was observed that this kind of installation helps in solving the leakage problems. However, for four-well cases, not all four wells can be sealed perfectly if the force applied over the chip surface is non-uniform.

As an alternative or addition to the grooves, a spacer may be placed on the upper surface of the polymer layer. The spacer may be of a ring-type, polygonal, or comparable design and surrounds the periphery of at least one well. The peripheral spacer functions as to alleviate the problems of leakage of the sample out of the reaction wells by providing an open space at the topmost portion of the well for gaseous fluids including bubbles to exit from the liquid reagent. Preferably the space provides for an additional 50 µm to about 500 µm in height though may be larger or smaller depending on the specific reaction. Also, most often the glass cover 32 is utilized with the peripheral spacer and in conjunction provides an enclosed volume for the accumulation of evolved gases from within the reaction well.

In an additional embodiment, the bubble problems are further resolved by an alternative cover for the reactor module of the PCR chip. Instead of using the full microscope cover slip to cover the reactor module (22 mm×22 mm), a quarter size of the original cover slip is used to only cover the small area above and around the PCR well in the reactor module. The smaller size of the glass cover can significantly reduce the leaking effects of the uneven surface of the fabricated reactor module since it is very difficult to obtain a completely flat and smooth reactor module surface with the current fabrication conditions.

Also alternatively, instead of a glass cover, a layer of mineral oil is provided on top of the sample in each of the reaction wells. This is used to prevent evaporation of the sample and also avoids the bubble problem. Other types of oil, such as silicon oil, can also be used. Any type of transparent, non-aqueous, unreactive solution having a refractive index close to the fluid in the sample so as not to cause any distortion effects, and having a high boiling point may be used as a sealant.

Figure 6:
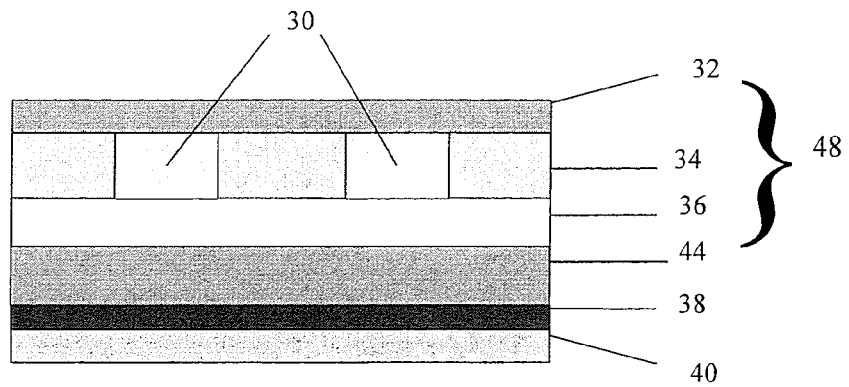
FIG. 6 is a cross-sectional view of the layer structure of the PCR chip with an additional chip substrate layer.

To easily adapt to different PCR thermal conditions required by different DNAs, the embodiment of the PCR chip, as shown in FIG. 1, is modified into a further embodiment as shown in FIG. 6. In this embodiment, a flat and smooth surface for a chip support substrate 44 can make it easier to hold the PCR chip without interrupting the film heater 38 position and provide a uniform thermal resistant condition at the interface between the reactor module 48 and heater 38. It can also prevent the chip from cracking, usually caused by irregularities in the surface of the reactor module 48. On the other hand, a temperature sensor, such as a thermocouple, can be put into the support substrate 44 to monitor the system temperature and thus control the thermal condition applied to the PCR chip.

Thermal cycling can be affected by the sizes of the reaction wells 30 and the reactor module 48 itself, as well as sizes and materials of the heater support substrate 40. Generally, when the sizes of the reactor module 48 and the well 30 are bigger, it takes longer to heat up and cool down the chip. Especially, the thickness of the chip significantly affects the thermal cycling. For the heater support substrate 40, if a material with low thermal conductivity is used, it takes longer to heat up and cool down the chip when the substrate size is bigger. However, when a material with high thermal conductivity is used, it takes a longer period of time to heat up the chip and takes a shorter period of time to cool down the chip. If a more powerful heater is available, adopting a bigger support substrate with a high thermal conductivity is encouraged since it can reduce the cooling time.

Chip size is decided based on the simulation results and the fabrication limits. Though it is desirable to make the chip as small and thin as possible to shorten the thermal cycling time, some problems occur when the chip is made too small. For example, if the chip is designed to be too thin, some shrinkage may occur while bonding the PDMS layer 34 onto the glass substrate 36 to form the reactor module 48. Leaks will then occur through the gaps caused by the shrinkage. If the chip is too narrow, it can cause the temperature distribution with the wells 30 to be less uniform because of the edge effects. An optimal design can only achieved by balancing the fabrication process, the chip installation and the theoretical predictions.

The heating and cooling module was designed and built as a miniature thermal cycler to provide different temperature levels required for PCR. In one embodiment, the cycler consists of a thin film heating element, such as a Pt micro-film resist heater, for heating, and a fan, such as a small computer CPU fan blowing from the side, for rapid cooling. A thin film heater is sandwiched between two thin metal substrates to form the heating element, and a thermocouple is placed between the top metal substrate and thin film heater to control the temperature of the top substrate by adjusting the heating power using the feedback information from the thermocouple. The heater sandwich and the thermocouple are bonded together to form a heating unit. The unit is then fixed onto a specially designed substrate. The reactor module has a size of 22 mm×22 mm×1 mm and weighs 0.6 g, as illustrated in FIG. 2. The reactor module 48 is placed on the top surface of the heater 38. Four screws are used to press the four corners of the reactor module to ensure good contact between the reactor module and the metal substrate. Alternative types of coupling means may be used and are readily understood by a person skilled in the art. The temperature control is accomplished by using a computer system through a data acquisition card (PCI-DAS 1001, Measurement Computing Corporation, Middleboro, Mass.).

Figure 7:
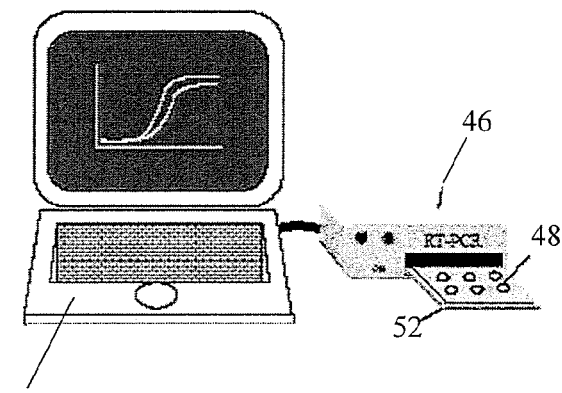
FIG. 7 is a diagram illustrating the system of one embodiment of the present invention.

As illustrated in FIG. 7, one embodiment of the system of the present invention consists of a reactor module 48, an optical detection module 46, and a control module 50. While the control module 50 is illustrated as being in a separate computer, it may be integrated directly into the optical detection module 46 using the appropriate hardware and software components. The reactor module 48 is placed on top of a micro thermal cycler platform 52 which is also integrated into the optical detection module 46. The thermal cycler platform 52 hosts the reactor module 48 and provides periodic heating and cooling (fan not shown) to the sample recipient. The credit-card sized reactor module 48, as described above, is a thin plastic plate with small reaction wells and a glass cover plate to prevent contamination and allow optical detection. The optical detector module 46 consists of micro-laser diodes, fiber optics, micro silicon photodiode detectors, optical filters, and an optical switch. The control module 50 contains electronic circuits and micro-chips to control the thermal cycling required for the PCR and to synchronize the operation sequences of the individual laser diodes, photo-detectors, and the optical switch, and provides an interface for computer control and data acquisition. During operation, the wells in the reactor module 48 are filled with the test sample and PCR solution. The reactor module 48 is coupled with the thermal cycler 52. After the thermal cycler platform 52 retreats into the detection unit and the power switch is turned on, the thermal cycling starts and the PCR reaction begins. The optical detection module 46 monitors the fluorescent signals in each well and the laptop computer 50 records the signal intensity. A fan 84 is also used in the thermal cycling. The results are analyzed and displayed on the monitor in real time.

Figure 8:
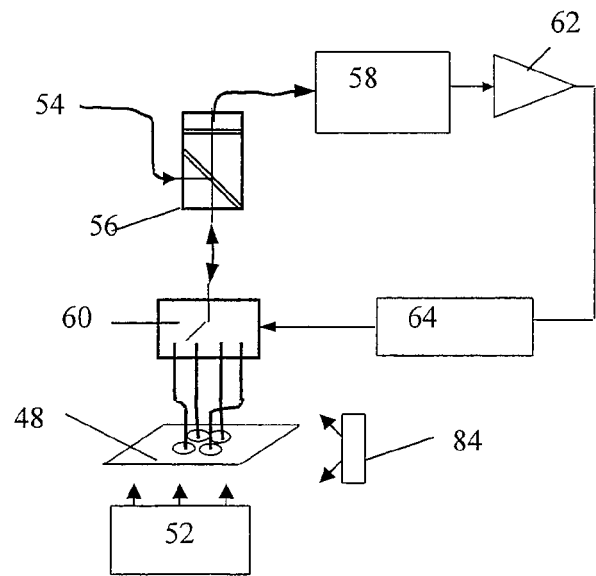
FIG. 8 is a schematic diagram of the optical detection module in accordance with an exemplified embodiment.

A 4-well miniaturized fluorescence detection system with laser, optical fiber and optical switch is illustrated in FIG. 8. This detection system consists of a laser 54, a filter cube 56, an optical switch 60 and a photo-detector 58. These four components are connected by optical fibers. The system is designed to use as few components as possible to reduce the overall size, and is capable of function expansion. The light from the laser 54 is input into a filter cube 56, the laser light is reflected by the filter cube 56 and coupled into the input port of a 1×4 optical switch 60. There are 4 ports on the output side of the optical switch 60, the input port can be connected to any one of the output ports by a program, controlled by computer 64. The four output fibers of the optical switch 60 are mounted above the four wells of the reactor module 48. They launch excitation light and, in the meantime, collect the fluorescence emissions from the reaction wells. The collected fluorescence emissions pass back through the optical switch 60 and the filter cube 56, and reach the photo-detector 58. Following the detector 58 is an electrical operation amplifier 62. Its output is fed to the computer 64 which also controls the optical switch 60 and thermal cycler temperature.

The fiber coupled filter cube 56 is a receptacle style fiber coupled filter cube. It is similar to a traditional filter cube used in a fluorescence microscope. The differences are that (1) there are two filters inside the cube, (2) three ports are equipped with multimode fibers. There are three filters in traditional microscope filter cubes, which include: exciter (excitation filter), dichroic filter and emitter (emission filter). Since lasers are used as excitation sources instead of broadband mercury lamps, an excitation filter is not necessary. Lenses are equipped with each of the three ports to collimate and/or focus the laser or fluorescence beam into/from the fiber. The focal point of the three leases are conjugated.

Figure 9:
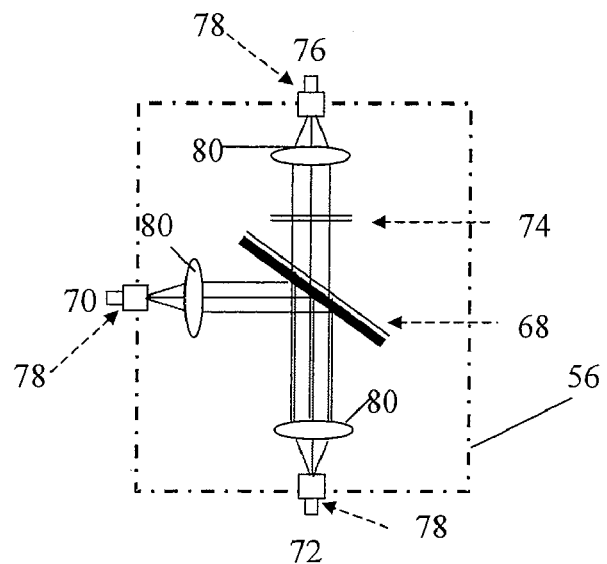
FIG. 9 is a diagram illustrating the working principle of the filter cube.

The principle of the fiber coupled filter cube is illustrated in FIG. 9. A dichroic filter 68 vertically reflects laser wavelength and directly transmits fluorescent wavelength. Laser light is input into the device from "Laser port" 70. It is vertically reflected by the dichroic filter 68 and output to the device from "Com port" 72. This laser light excites the fluorescence in the sample through the fiber at "Com port" 72 and the fiber also collects the fluorescence light produced by the sample. The fluorescence light passes through the dichroic filter 68 and finally reaches the detector. Laser light can also be reflected at the fiber end of the "Com port" 72; about 2% reflected laser light passes through the dichroic filter 68, which represents the noise level of the system. So, a band pass filter 74 is inserted into the "Fluorescent port" 76 to remove this portion of laser light. The dichroic filter 68 and emitter are bought from Chroma Inc, they are especially designed for Cy5 or Alexa Fluor 647™ dye. Filter package with fiber has been done by OZ Optics Inc. Fiber connectors 78 are present at each of the Fluorescence port 76, Laser port 70, and Com port 72. Lenses 80 are used to collimate the beams.

In order to collect more fluorescent signals (leading to higher detection sensitivity), 200 µm or 400 µm multimode glass fibers were considered after theoretical calculation and investigation of similar opto-electrical systems were made. Compared with 200 µm fiber, 400 µm fiber can acquire more fluorescence. However, considering the size, mechanical flexibility, compatibility with other components in the system, 200 µm fiber was selected for use. Criteria for selecting lasers in this system include high power, small footprint and suitable wavelength. A semiconductor laser is the best choice due to its inherent small dimension. The lowest wavelength range of the commercial semiconductor laser is 630~650 nm. Thus, Alexa Fluor 647™, one of the latest, high performance dyes with the highest extinction coefficient, was selected as reporter dye in the real-time PCR, with a peak excitation wavelength of 650 nm. For the photo detector, compared with other types of detectors such as APD (analog photo-detector), PMT (photo-multiplier tube) and CCD (charge-coupled device), PIN (P-Intrinsic-N), which has the smallest size, was selected. In order to enhance the fluorescence collecting efficiency, minimize the number of components and reduce the footprint of the optical detection system, a fiber-coupled filter cube was designed and developed.

As previously mentioned, during real-time PCR, the optical detection system must monitor the fluorescence intensity in real time. The key is to identify the thermal cycle number at which the reporter dye emission intensities rise above background noise and start to increase exponentially. This cycle number is called the threshold cycle, $C_t$. The $C_t$ is inversely proportional to the number of starting copies of the DNA sample in the original PCR solution. Knowing $C_t$, the quantity of the DNA to be detected in the sample can be determined.

At least one set of excitation-detection wavelength pair must be available at each PCR well to identify both the species in each well. To increase the number of samples detected without increasing the number of wells, additional sources and detectors may be provided. For example, if two sources and two detectors are provided, the system can detect different wavelengths being emitted from a common well simultaneously.

As per FIG. 8, the multiplexing is made possible by using an optical fiber light transmission-switching system, for which switching components are known to a person skilled in the art. This embodiment requires two light sources and two detectors. Different excitation lights can be applied to all the wells following the specified sequence. The optical switch allows the emission light from different wells to be monitored by the filter-detector corresponding to the excitation light source according to the specified sequence. This way, the number of light sources and detectors are independent of the number of wells, and smaller wells may be employed. In addition, fiber optic technology permits effectively limitless multiplexing, which permits more reactant wells and more light interactions with little increase in infrastructure. To create this multiplexing, the switch preferably has at least as many ports as reaction wells on the side of the optical switch in closest communication with the reaction module. For example, a four well reaction module should correspond to an optical switch with at least four ports on the side of the switch in closest communication with the reaction module. In additional embodiments, the optical fiber light transmission-switching system may include multiple optical switches as well as switches with a multitude of ports, some ports not always in use, especially with reaction modules having fewer wells.

In order to operate, the optical detection system must be capable of switching the optical paths between wells, and between the specific pairs of the laser diodes and photodiode detectors. This requires that the micro-laser diodes, micro-photodiode detectors, optical filters, and optical switch be synchronized and controlled electronically. Therefore, an electronic device was developed and used for this purpose. In addition, the optical detection system must be synchronized with the PCR controlling device so that both the PCR and the fluorescent detection will operate under the specified sequence. The controlling devices can provide an interface for computer control and data acquisition.

Simulation and temperature measurement with both thermocouple and Rhodamine B dye have shown that the present invention can provide a temperature profile of three different temperature levels required by the three steps of the PCR (Polymerase chain reaction), such as, denaturation, annealing, and extension steps.

In order to further illustrate the principles and operation of the present invention, the following examples are provided. However, these examples should not be taken as limiting in any regard.

EXAMPLE 1

Comparative PCR Tests with Reactor Module and Miniature Thermal Cycler (Chip System), and Commercial PCR Machine Three kinds of DNA template are used to test the chip system. They are human genomic DNA(2054), BAC (DJ0416J11) DNA and *E. coli* O157:H7 DNA.

BAC is an abbreviation of bacterial artificial chromosome. Here, BAC(DJ0416J11) DNA is constructed by insertion of genomic DNA fragments corresponding to the genomic DNA amplified in the current experiment, into a vector, which can be replicated in a bacterial host. This has many advantages:

rapid growth of the host, high stability of the DNA fragment when inside the host, few chimeric clones, easy and rapid purification of the BAC DNA, and large amounts of sequenced BAC clones.

The different DNA is tested at different protocols, as shown below.

TABLE 1

Reagents of PCR mixture for human genomic DNA (2054)

| Components | Volume (μL 1x) |
|---|---|
| DNA(100 ng/μL) | 1 |
| 10xbuffer | 2.5 |
| DNTP(2.5 mM) | 2.0 |
| $MgCl_2$ | 0.75 |
| Primer (forward + backward) | 1 |
| Taq | 0.3 |
| DI-water | 17.45 |

TABLE 2

Reagents of PCR mixture BAC (DJ0416J11) DNA

| Components | Volume (μL 1x) |
|---|---|
| DNA(100 ng/μL) | 1 |
| 10xbuffer | 2.5 |
| DNTP(2.5 mM) | 2.0 |
| $MgCl_2$ | 0.75 |
| Primer (forward + backward) | 1 |
| Taq | 0.3 |
| DI-water | 17.45 |

TABLE 3

Reagents of PCR mixture for E. coli O157:H7 DNA

| Components | Volume (μL 1x) |
|---|---|
| DNA(2.4 ng/μL and 0.12 ng/μL) | 1 |
| 10xbuffer | 2.5 |
| DNTP(2.5 mM) | 2.0 |
| $MgCl_2$ | 0.75 |
| Primer (forward) | 0.3 |
| Primer (backward) | 0.3 |
| Taq | 0.25 |
| DI-water | 17.9 |

For the human genomic DNA (2054) and BAC (DJ0416J11) DNA, the following thermal condition is used:
Initial denature: 94° C. for 60 seconds
Initial annealing: 59° C. for 30 seconds
Initial extension: 72° C. for 30 seconds
    35 cycles (30 cycles for J11 DNA) of:
Denature: 94° C. for 30 seconds
Annealing: 59° C. for 30 seconds
Extension: 72° C. for 30 seconds
For the E. coli O157:H7 DNA, the following thermal condition is used:
Initial denature: 95° C. for 10 minutes
Initial annealing: 54° C. for 30 seconds
Initial extension: 72° C. for 60 seconds
    45 cycles of:
Denature: 94° C. for 20 seconds
Annealing: 59° C. for 30 seconds
Extension: 72° C. for 60 seconds
At the same time, to compare the amplification results, PCR tests using a commercial PCR machine are also carried out.

After running PCR tests either with the PCR chip system or with a commercial PCR machine, agarose gel electrophoresis of DNA is conducted to check whether the designed PCR process was successfully achieved. The details of the agarose gel electrophoresis procedure are generally known to those skilled in the art. Briefly, 0.5% Tris-borate-EDTA (TBE) is used as the buffer, bromophenol blue and xylene cyanol dyes are used as the tracking dyes, and DNA fragments are visualized by staining with ethidium bromide and placing the gel on a ultraviolet transilluminator. For the agarose gel electrophoresis system, FB300 DC power supply (FisherSci, CA) and gel box (Model QSH, international Biotechnologies Inc, USA) are used to run the gel and the Versa Doc imaging system (Bio-Rad Laboratories, USA) is used to take the picture of the gel results.

The designed PCR chip system can successfully amplify three different kinds of DNAs: human genomic DNA(2054), BAC (DJ0416J11) DNA and E. coli O157:H7 DNA. For E. coli O157:H7, the primers amplify the stx1 (150 bp) gene of E. coli O157:H7. For the BAC (DJ0416J11) DNA and genomic DNA (2054), the primers are used to amplify the specific (230 bp) gene of the human genomic DNA.

Figure 17:
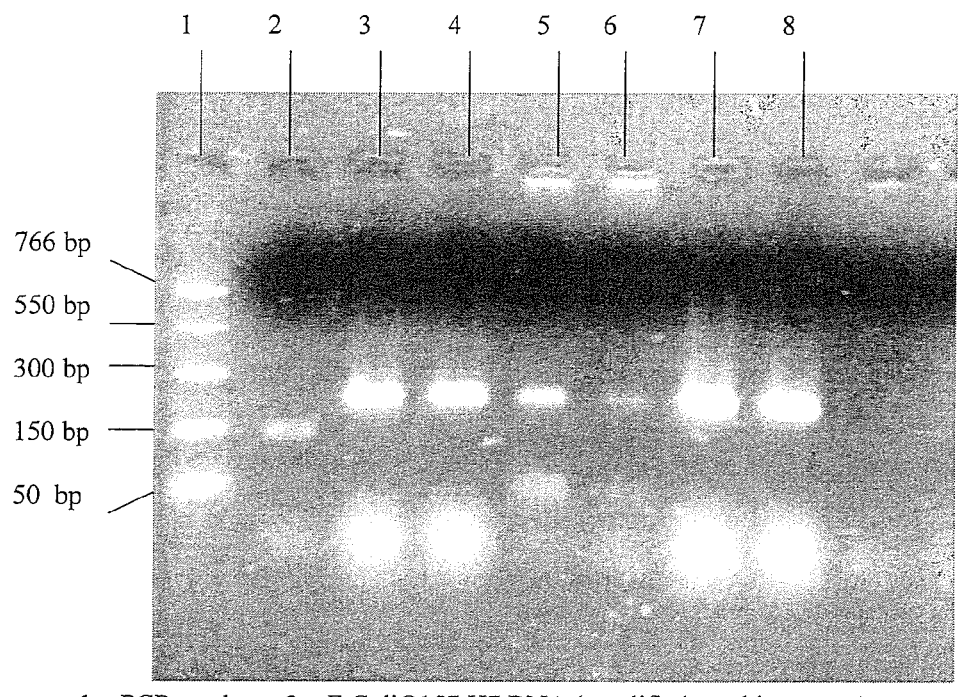
FIG. 17 illustrates the results of PCR tests with different DNA using the chip system compared to a commercial PCR machine.

FIG. 17 depicts the results observed after running the Agarose gel for the three amplified DNAs. In FIG. 17, lane 1 is the reference strand generated by using PCR marker and other strands are PCR products from different DNAs and PCR systems. Lane 2 is the PCR product of stx1 (150 bp) gene of the E. coli O157:H7 DNA tested on the chip system, lane 3&4 are the PCR products of the BAC (DJ0416J11) DNA tested on the chip system, lane 5&6 are the products of the genomic DNA(2054) tested on the chip system, and lane 7&8 are the products of the BAC (DJ0416J11) DNA. Lane 5 is the product of genomic DNA on the chip comprising a reactor module with 1% PVP (polyvinylpyrrolidone) coating, and lane 6 is the product of genomic DNA on the chip comprising a reactor module without PVP coating. As shown in FIG. 17, for the E. coli O157:H7 DNA, the DNA fragment stx1 (150 bp) is observed at the 150 bp region referring to the PCR marker, and for the BAC (DJ0416J11) DNA and genomic DNA, 230 bp genes are observed as expected since the primer was designed to amplify the product of 230 bp gene of the genomic DNA. Both the BAC DNA and genomic DNA have the same PCR product because the BAC (DJ0416J11) DNA is constructed with insertion of the same DNA fragment ranges of the genomic DNA used in this project.

In FIG. 17, the signal of the products of the BAC (DJ0416J11) DNA is much stronger than that of the genomic DNA. It is because, in the same amount of DNA, there are much more of the specific gene fragments in the BAC (DJ0416J11) DNA than occurs in genomic DNA. This means that there are more initial copies of DNA template strand in the BAC (DJ0416J11) DNA PCR mixtures. Comparing lane 3&4 with lane 7&8, it is shown that for the BAC (DJ0416J11) DNA, the chip PCR system can generate PCR products as efficiently as the commercial PCR machine. FIG. 17 also demonstrates that the signal for the product of the genomic DNA in lane 5 is stronger than that in lane 6. This implies that the PVP coated reactor module results in a better PCR product than the chips containing PCR reactor modules without this coating.

Difficulties are encountered in amplifying the human genomic DNA in the designed chip system. Because the materials of the PCR reactor module are different from the material of the commercial PCR tubes, it is necessary to check the effect of the material of the reactor module on the PCR process. Our reactor modules were made of PDMS and glass and the commercial PCR tubes were made of plastic. It is known that glass can inhibit the PCR process for some DNA. Experiments are conducted to verify the effect of glass on the PCR process for the human genomic DNA.

In one experiment, a small piece of glass is placed into the commercial PCR tubes and the PCR reaction is run on the commercial PCR machine with the human genomic DNA. In those cases, there are no PCR products observed when the DNA gel electrophoresis is carried out after the PCR process. This implies that the glass inhibits the PCR process of the human genomic DNA. Since it is reported that PVP coating could eliminate the glass inhibition of the PCR process of the genomic DNA [Detlev Belder and Martin Ludwig, Surface Modification in Microchip Electrophoresis, Electrophoresis, 2003, 24, 3595-3606; Nicole J. Munro, Andreas F. R. Huhmer, and James P. Landers, Robust Polymeric Microchannel Coating for Microchip-Based Analysis of Neat PCR Products, Analytical Chemistry, 2001, 73, 1784-1794] the reactor module and cover glasses are coated with PVP solution, are washed with DI-water, and the PCR test is then conducted with the genomic human DNA.

Figure 18:
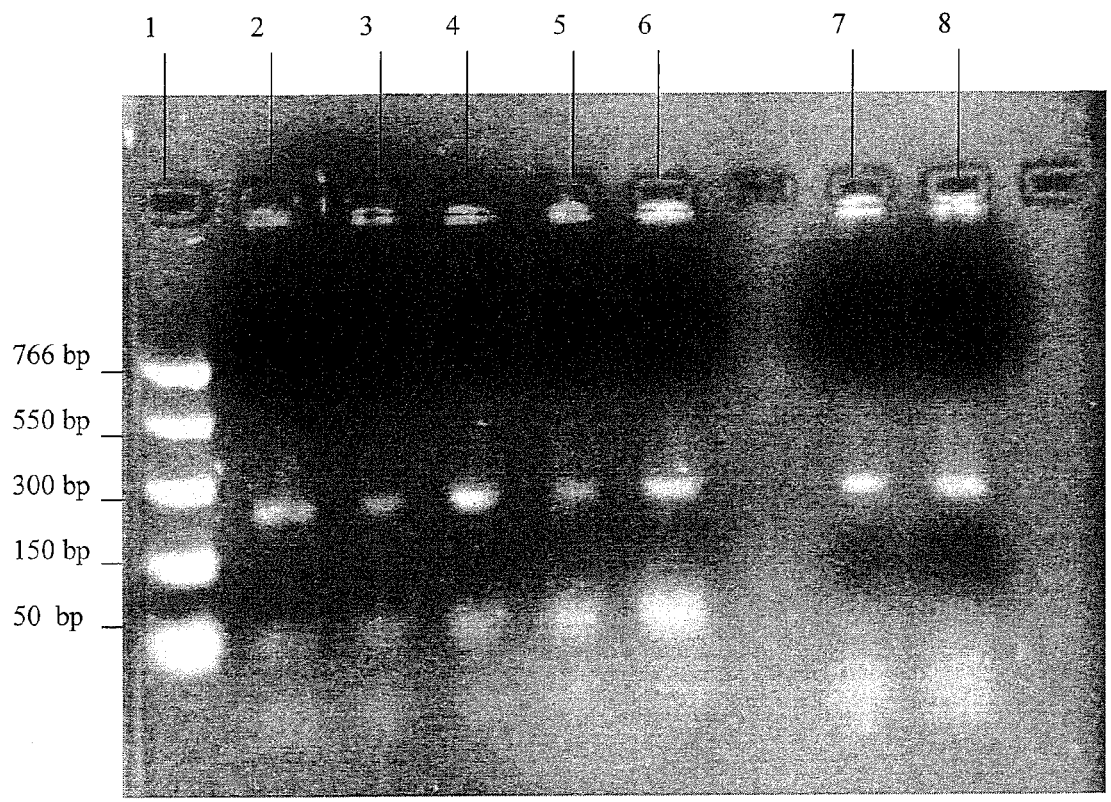
FIG. 18 illustrates the results of PCR tests with genomic DNA (2054) under different conditions with the chip system.

The PCR products are detected using gel electrophoresis and the results are shown in FIG. 18. In FIG. 18, lane 1 is the reference strand which is generated by using PCR marker, lanes 2 to 6 are the PCR products obtained from the PCR tests using the reactor modules with PVP coating, and lanes 7 and 8 are the PCR products obtained from using the commercial PCR machine. It clearly shows that all five tests generate positive PCR product. Therefore, the PVP coating minimizes the non-specific adsorption of human genomic DNA on the surface of the reactor module, which is comprised of glass and PDMS.

EXAMPLE 2

Real-time PCR on a Disposable PDMS Reactor Module with a Miniaturized Thermal Cycler The reactor module for use in this example comprises two layers of PDMS, bonded onto a 22×22×0.1 mm glass substrate (VWR International). The bottom layer is for making a reaction well, and the top layer is for holding mineral oil which covers the reactants to prevent evaporation. Liquid Sylgard 184™ (Dow Corning, Michigan, USA) is thoroughly mixed with curing agent in a weight volume ratio of 15:1. A constant amount of the mixture is then poured into a rectangular mold, in order to create PDMS sheets of constant thickness for fabrication of the PCR reactor modules. The thickness of the PDMS sheets is determined by the height of the mold and is 0.4 mm in this Example.

After curing for approximately 3 hours at 75° C., the PDMS sheets are removed from the mold, cut down to the same size as the substrate glass, and a through hole is punched in the center of the PDMS sheet with a metal puncher to form a reaction well. In this example, chips with different well sizes, 3 mm, 2 mm and 1 mm in diameter, are fabricated. The substrate glass of 0.1 mm thickness is coated with a thin layer of PDMS, because, as previously mentioned, glass is an inhibitor of PCR. The coated glass and PDMS sheet are oxidized in a plasma discharger (PDC-32G, Harrick Scientific, USA) for 60 seconds, and then brought together for bonding. Reactor modules with multiple wells are fabricated similarly by punching multiple holes in the PDMS sheets.

To substantially prevent evaporation of the reaction mixture, mineral oil is used to cover the reaction well. Another PDMS sheet with thickness of 0.5 mm is fabricated and is cut down to 10 mm×10 mm. The through-hole in the center is 7 mm in diameter. After a 60 seconds plasma treatment, this sheet is bonded to the PCR chip and centered with the reaction well to contain the pool of oil.

Figure 19:
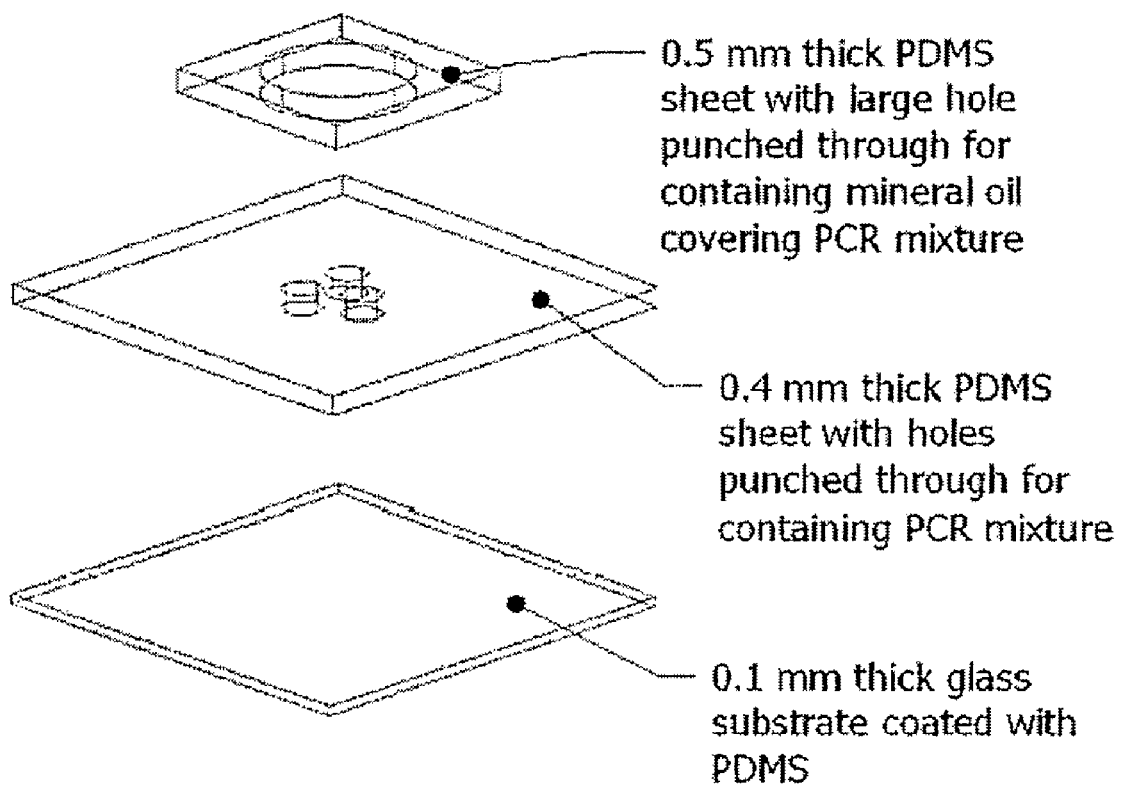
FIG. 19 shows schematically the assembly of a multiple-well reactor module in accordance with one embodiment of the invention.

To demonstrate the concept of multiple PCR wells on a single chip, three holes of 1 mm diameter are punched on the bottom PDMS sheet of the chip. The center of these three holes forms an equilateral triangle. The distance between holes is about 200 μm. Three wells are selected because of the limitation of the maximum field of view of our particular fluorescence microscope objective lens. From the heater and chip size point of view, there is no such limitation. FIG. 19 shows schematically the assembly of a multiple-well PCR chip.

A specific DNA segment, a 150-bp segment of *E. coli* O157:H7 stx1 is amplified by using TaqMan™ polymerase. *E. coli* DNA was extracted from cells using the protocol and reagents from the QIAGEN Blood and Cell Culture DNA Kit. The primer set (Gene Link, Hawthorne, N.Y.) is: forward, 5'-GAC TGC AAA GAC GTA TGT AGA TTC G-3' (SEQ ID NO:1), and reverse, 5'-ATC TAT CCC TCT GAC ATC AAC TGC-3' (SEQ ID NO:2). The TaqMan™ probe (Gene Link, Hawthorne, N.Y.) is labeled with AlexaFluor 647™ reporter dye and BHQ3™ quencher dye with the following sequence: AlexaFluor 647™ 5'-TGA ATG TCA TTC GCT CTG CAA TAG GTA CTC-3' BHQ3™ (SEQ ID NO:3). The excitation and emission peaks of AlexaFluor 647™ are 650 nm and 670 nm, respectively.

Every 100 μl PCR mixture contains 10 μl of 10× buffer, 1.2 μl of each primer (25 μM), 2.0 μl of probe (10 μM), 8.0 μl of dNTPs (0.625 mM of each), 3.0 μl of $MgCl_2$, 1.0 μl of TaqMan™ polymerase (5 U/μl) and an appropriate volume of $H_2O$ and DNA template. Each cycle comprises of three stages: denaturing at 94° C. for 20 seconds, annealing at 55° C. for 30 seconds, and extension at 72° C. for 30 seconds. Each PCR run begins with a hot start at 94° C. for 5 minutes, and ends with a final extension at 72° C. for 10 minutes.

The volumes of the 3 mm, 2 mm and 1 mm diameter reaction wells are 7 μl, 3 μl and 0.9 μl respectively. Choosing the 7 μl and 3 μl PCR wells is, on one hand, to prove that the PCR reactor module is flexible and can amplify DNA with different volumes of PCR mixture, and on the other hand, to allow verification of the PCR results by gel electrophoresis which requires a sufficiently large volume. Although real-time PCR is conducted in the experiments and fluorescence detection is done for every PCR run, gel electrophoresis is conducted to confirm the correct size of PCR product and no formation of primer dimers. The use of the gel electrophoresis is simply a proof of concept and is not necessary for the techniques of the present invention. The well volume of the gel pad is 10 μl so a relatively larger volume of PCR wells is necessary. A 2% agarose gel with 0.04% ethidium bromide is used and the results are visualized with a UV camera (Bio-Rad Gel Doc 1000™, Bio-Rad Laboratories, Hercules, Calif.).

Figure 16:
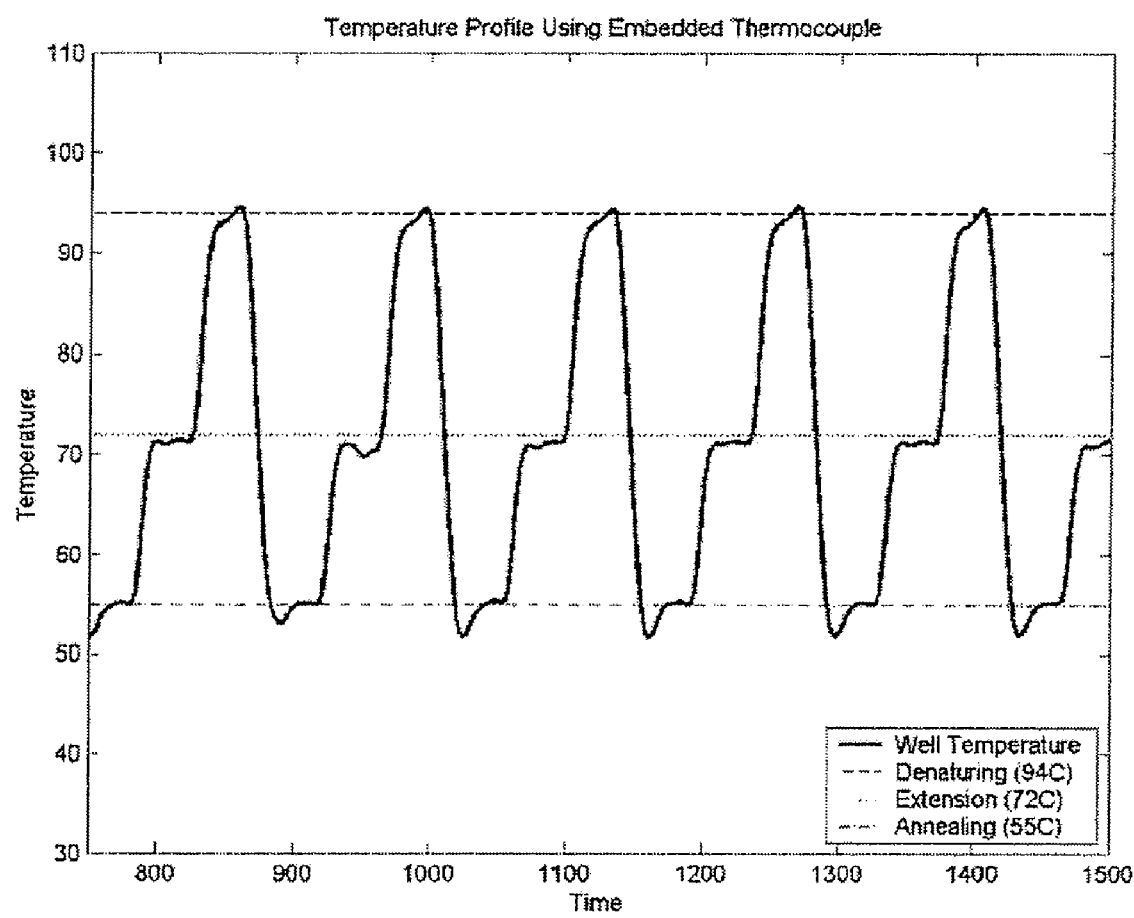
FIG. 16 illustrates the actual cycling temperature in the well of a single-well reactor module in an experiment for E. coli O157:H7 stx1 PCR.

The experiments presently described are conducted using a miniature thermal cycler which was designed and built to provide different temperature levels required for PCR, as previously disclosed. The liquid temperature in the reaction well is lower than that of the substrate, and is calibrated by using a calibration reactor module with another thermocouple embedded directly in the reaction well. By adjusting the temperature of the substrate, the ideal temperature profile in the reaction well can be obtained. FIG. 16 presents the cycling temperature in the well of a single-well reactor module in the experiment for *E. coli* O157:H7 stx1 PCR. The ramping-up time from 55° C. to 72° C. and from 72° C. to 94° C. is about 6 sec, and 20 sec from 94° C. down to 55° C. The temperature holds 20 sec at 94° C. for denaturing, 30 sec at 72° C. for extension and 30 sec at 55° C. for annealing.

For each PCR run, a newly fabricated reactor module is clamped onto the thermal cycler substrate; PCR mixture is placed into the reaction well of the PCR reactor module; and the top of the reaction well is covered with mineral oil. The thermal cycling program is executed and the fluorescent intensity of the PCR mixture is monitored as the reaction progresses.

As described above, the developed miniature thermal cycler can be mounted on the stage of any standard fluorescence microscope to measure the fluorescence intensity for real-time PCR.

Fluorescent images of the sample well are taken by a fluorescence microscope (TE2000™, Nikon Inc.) with CCD camera (Qimaging, Vancouver, B.C.) during each PCR run in the experiments. This fluorescent microscope is equipped with image analysis software (SimplePCI™) that allows the calculation of the average fluorescent intensity of any selected area of the image. Excitation light of 650 nm is provided through a 4× microscope objective lens and the image is captured once every 6 seconds. Due to the slight temperature dependence of the reporter dye, different intensity levels are observed to occur at different stages of PCR. For the results of this work, the mean intensity during annealing (55° C.) is used to represent the fluorescence intensity of each cycle since the greatest intensity change occurs at this temperature level.

Real-time monitoring of PCR can be used for both detection of a specific type of DNA and quantification of template DNA concentration. To verify the proposed micro thermal cycler and reactor module system, several PCR experiments are completed. The experiments use TaqMan™ polymerase chain reaction techniques to amplify the stx1 segment of $E.\ coli$ O157:H7. As described above, its length is approximately 150-bp. The results demonstrate that this system can generate the correctly amplified PCR product and perform complete real-time PCR detection with different volumes of the PCR solution. Additionally, multiple real-time PCR experiments can be done simultaneously using multiple-well reactor modules.

Figure 10:
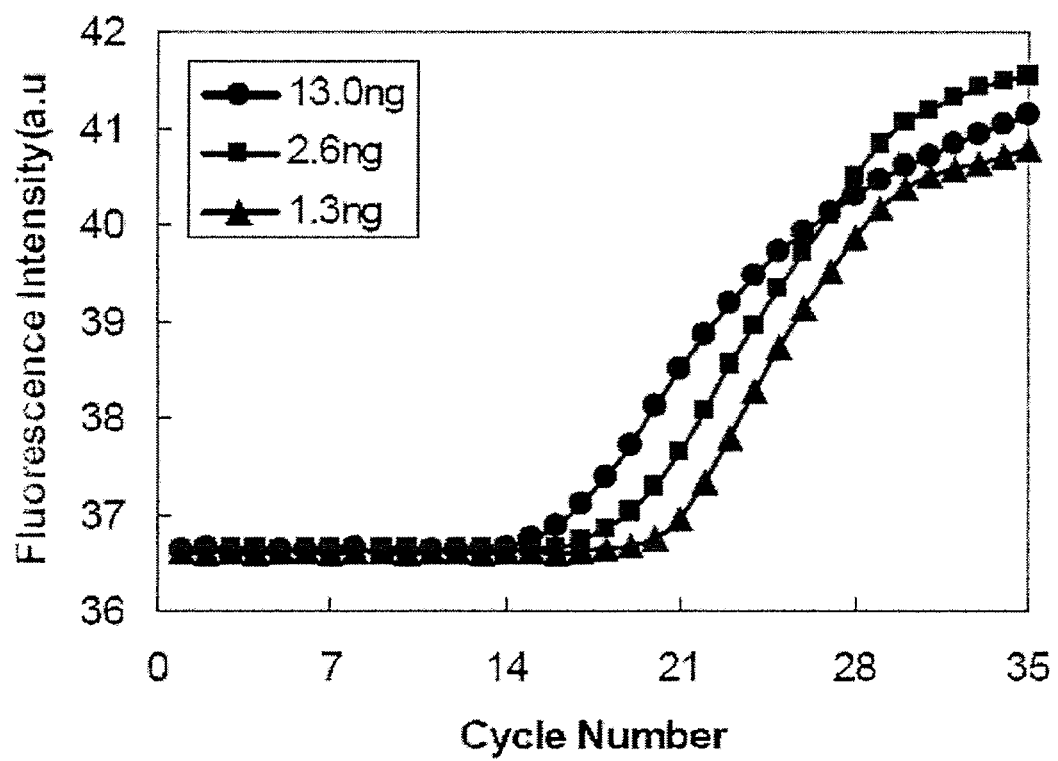
FIG. 10 is a graph of the fluorescence intensity of three runs of real-time PCR having different initial DNA templates.

For single-well reactor modules, real-time PCR tests with different reaction volumes (7 µl, 3 µl and 1 µl) of reagent mixture and different initial DNA concentrations are conducted and the fluorescent intensity at each cycle of PCR is measured. In order to demonstrate that the 150-bp stx1 segment could be successfully amplified, real-time PCR experiments with a 7 µl reaction volume are completed. This relatively large reaction volume is required for verification of PCR product size using gel electrophoresis. FIG. 10 shows the mean fluorescent intensity at each cycle, for different amounts of the template DNA (1.3 ng, 2.6 ng and 13.0 ng), and the same mixture volume of 7 µl. For all three amounts of DNA, the characteristic intensity curve is observed, indicating that the PCR was carried out successfully. During the initial phase, approximately the first 10 cycles, the intensity remains constant. Following this phase is a rapid increase in fluorescent intensity, followed by a plateau in the intensity level around the $30^{th}$ cycle. Based on the working principle of the TaqMan™ probe, the reporter dye, AlexaFluor 647™, light is emitted upon cleavage from the BHQ3™ quencher molecule after reproduction of the specific DNA segment, $E.\ coli$ O157:H7 stx1. Therefore as amplification proceeds, the fluorescent intensity increases. During the initial phase, although amplification occurred, the change in intensity was below the detection limit. After a certain number of cycles, the increase in the fluorescent intensity is detectable and exponential amplification is observed. Finally, the intensity reaches a plateau as reagents are fully consumed. Comparing the three cases shown in FIG. 10, it can be clearly seen that the measured fluorescent intensity starts to increase at a different cycle number for different amounts of initial DNA template. Although DNA quantification is not looked at here, the correct trend is shown in these results: A larger amount of initial template DNA corresponds to an earlier onset of the exponential phase, or an earlier detectable increase in intensity. The fluorescent intensity starts to increase at approximately the $15^{th}$ cycle in the case of 13 ng initial template DNA, the $18^{th}$ cycle for the case of 2.6 ng and the $20^{th}$ cycle for the case of 1.3 ng.

Figure 11:
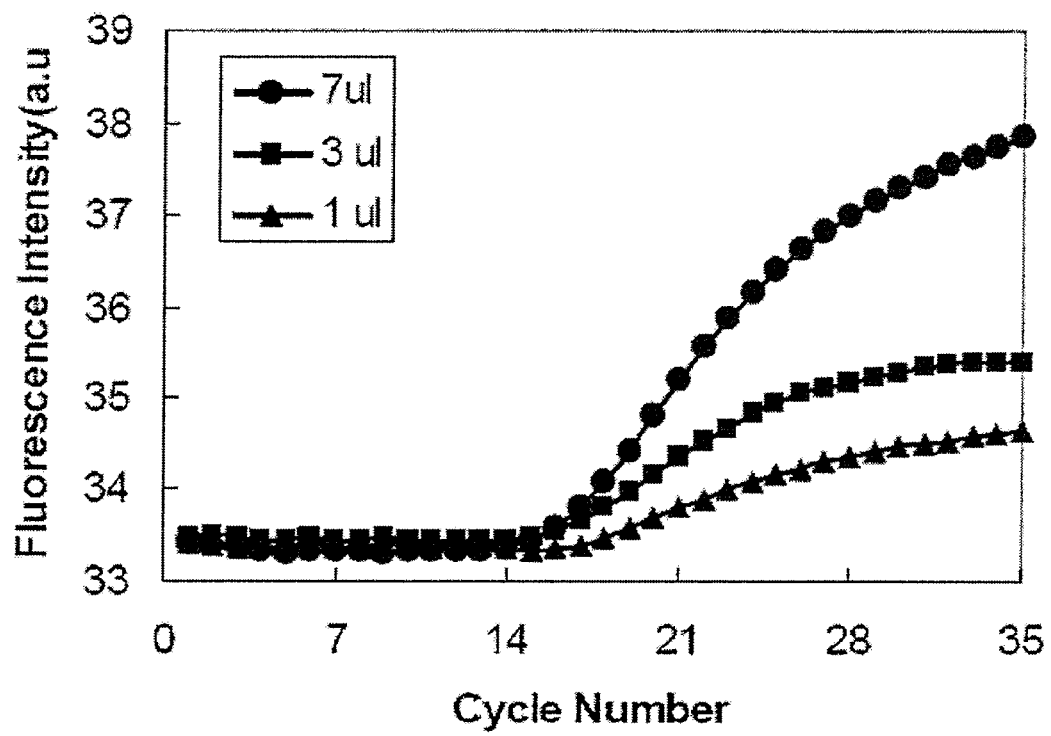
FIG. 11 is a graph of the fluorescence intensity of three runs of real-time PCR having different volumes of mixture, but the same initial DNA concentration.

It is desirable to have a smaller PCR mixture volume for reducing the cost of the reagents and samples and for increasing the number of wells per unit area of the reactor module. However, using a smaller PCR reaction well must ensure obtaining the correct real-time PCR intensity curves. FIG. 11 shows the measured fluorescent intensity curves of three tests with the same template DNA concentration, but different volumes (1 µL, 3 µL, and 7 µL) of the PCR mixture. As shown in this figure, a similar trend is present in all three cases, corresponding to the characteristic intensity curve described above. This implies the successful PCR in all three mixture volumes. Comparing the three curves shown in FIG. 11, the measured fluorescent intensity starts to increase at almost the same cycle number (i.e., the $15^{th}$ cycle) for all three cases but increases at different rates and reaches a plateau at different intensity levels. In these three cases the fluorescent intensity starts to increase at the same cycle number because they have the same concentration of initial template DNA. The different rates of the intensity increase are due to the lower contribution from the lower total of DNA copies and fewer reporter dye molecules associated with smaller volumes of PCR mixture.

Figure 12:
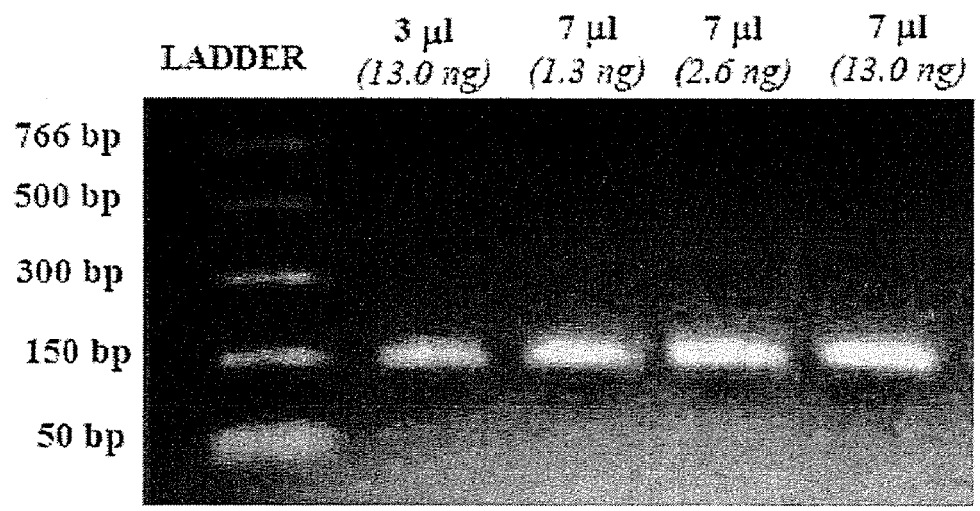
FIG. 12 is the gel electrophoresis results of 3 µl and 7 µl PCR mixture reactions.

To verify the PCR amplification results, gel electrophoresis is also used in this work. Due to the volume limitation, gel electrophoresis is conducted for only the 7 µl and 3 µl samples after each real-time PCR reaction. Typical results are shown in FIG. 12. Since the DNA sample of $E.\ coli$ O157:H7 stx1 is 150-bp, the gel results should show a distinct band that corresponds to the 150-bp marker in the PCR ladder. As shown in FIG. 12, the first column is PCR ladder, the second column is the gel electrophoresis result of a 3 µl PCR reaction, and the third to fifth columns are the results of the 7 µl PCR reactions. As expected, the bright band of PCR product for each sample corresponds to the marker's band at 150-bp. The gel result of the 3 µl sample is not as bright as the 7 µl samples due to the smaller mixture volume. The gel results further prove that amplification of the correct PCR product was achieved. For the 1 µl reaction, the total volume is too small to run gel electrophoresis. However, it is reasonable to assume that the 1 µl case presented in FIG. 11 has successful PCR amplification, as a similar fluorescent intensity curve is observed as for those of the 7 µl and 3 µl cases.

Figure 13:
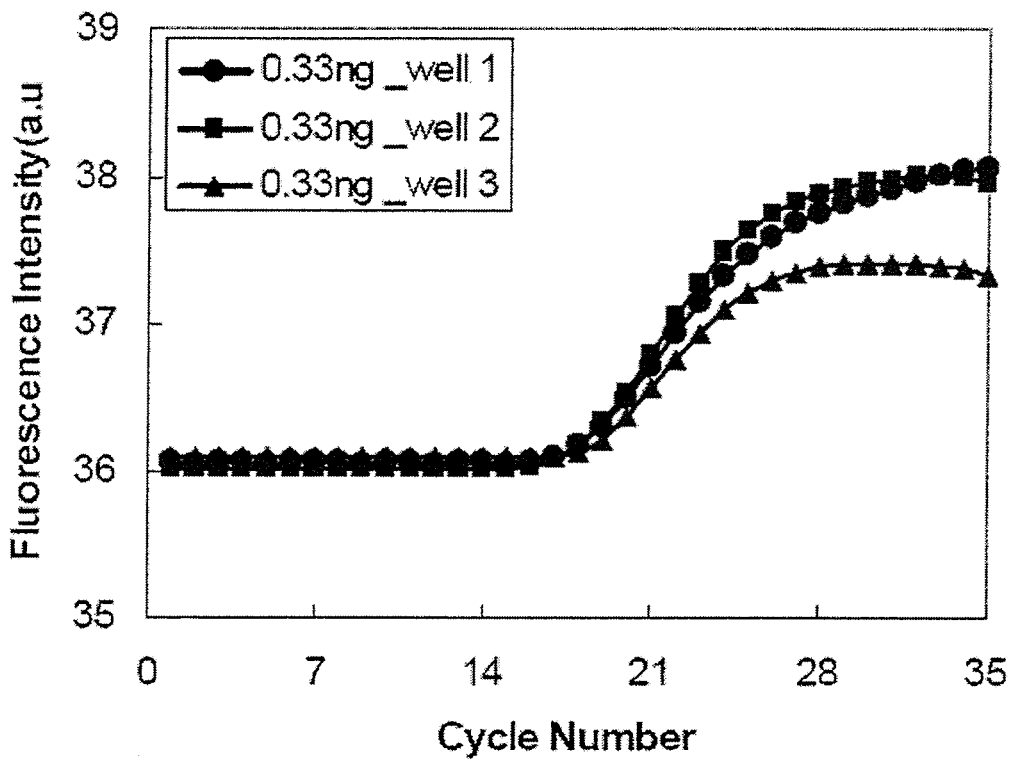
FIG. 13 is a graph of the fluorescence intensity from a three-well reactor module where each well has the same DNA template amount.
Figure 14:
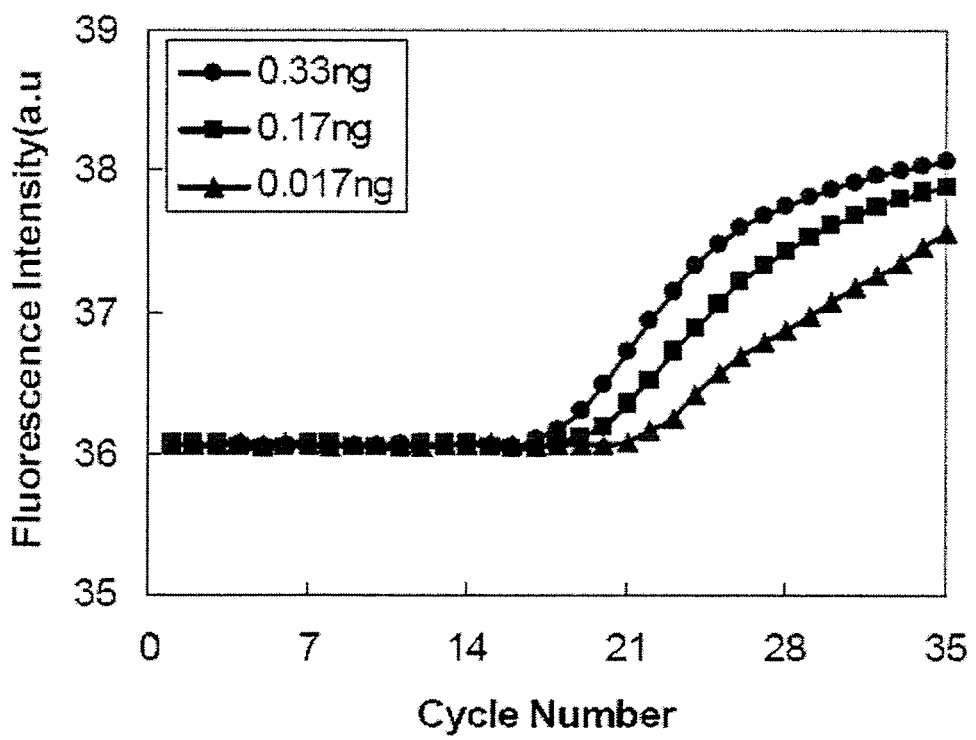
FIG. 14 is a graph of the fluorescence intensity from a three-well reactor module with different template DNA concentrations in each well.

Multiple concurrent reactions can validate the repeatability of the same PCR protocol, or can be used to complete the serial dilution curves required for the quantification of the amount of DNA in the sample in a more efficient manner. Since it is already shown that smaller reaction volumes, such as 1 µl, could successfully achieve amplification in the present system, this small volume is used to carry out multiple-well PCR tests. Three-well reactor modules are tested in this experiment because the microscope objective lens we have could only cover an area of three wells, though it is possible to design and fabricate reactor modules with more wells for use with alternative detection systems. In the experiments, a volume of 0.9 µl reaction mixture is applied to each well in the 3-well reactor module. During each PCR run, the fluorescent intensity of each well is monitored using the fluorescent microscope and the results are shown in FIG. 13 and FIG. 14. FIG. 13 shows the fluorescent intensity results of three simultaneous reactions that have the same initial DNA concentration of 0.33 ng/0.9 µl, verifying the repeatability of the PCR protocol and the system. FIG. 14 presents the fluorescent intensity results of three simultaneous reactions that have different initial DNA concentrations. As shown in both FIG.

13 and FIG. 14, all intensity curves of the tested cases have the characteristics of successful PCR amplification. Similar to the results of single well reactor modules, for the cases with the same initial concentration of a template DNA of 0.33 ng/0.9 µl, the measured fluorescent intensity starts to increase at almost the same cycle number, the 18$^{th}$ cycle, for all three cases shown in FIG. 14. The concentration of 0.33 ng/0.9 µl for the curves in FIG. 13 corresponds to the concentration of 2.6 ng/7 µl in FIG. 10. The critical cycle numbers for these two samples are indeed the same, i.e., the 18$^{th}$ cycle. Additionally, the fluorescent intensity starts to increase after different cycle numbers for different initial amount of template DNA, as shown in FIG. 14. The DNA concentration of the samples in FIG. 14 is 0.33 ng/0.9 µl, 0.17 ng/0.9 µl, and 0.017 ng/0.9 µl, and the critical cycle numbers are the 18$^{th}$, 19$^{th}$, and 21$^{st}$, respectively, for the three cases. Comparing the initial DNA concentration and critical cycle number of PCR runs conducted in the multiple-well reactor module in FIGS. 13 and 14 and the single-well reactor module in FIGS. 10 and 11, the results indicate that the multiple-well PCR reactor module does not show less efficiency than a single-well reactor module although the volume is reduced. This also indicates that the multiple-well PCR is repeatable, and can be used to generate simultaneous serial dilution curves for quantification.

EXAMPLE 3

PCR Test with Miniaturized Fluorescence Detection System

Figure 15:
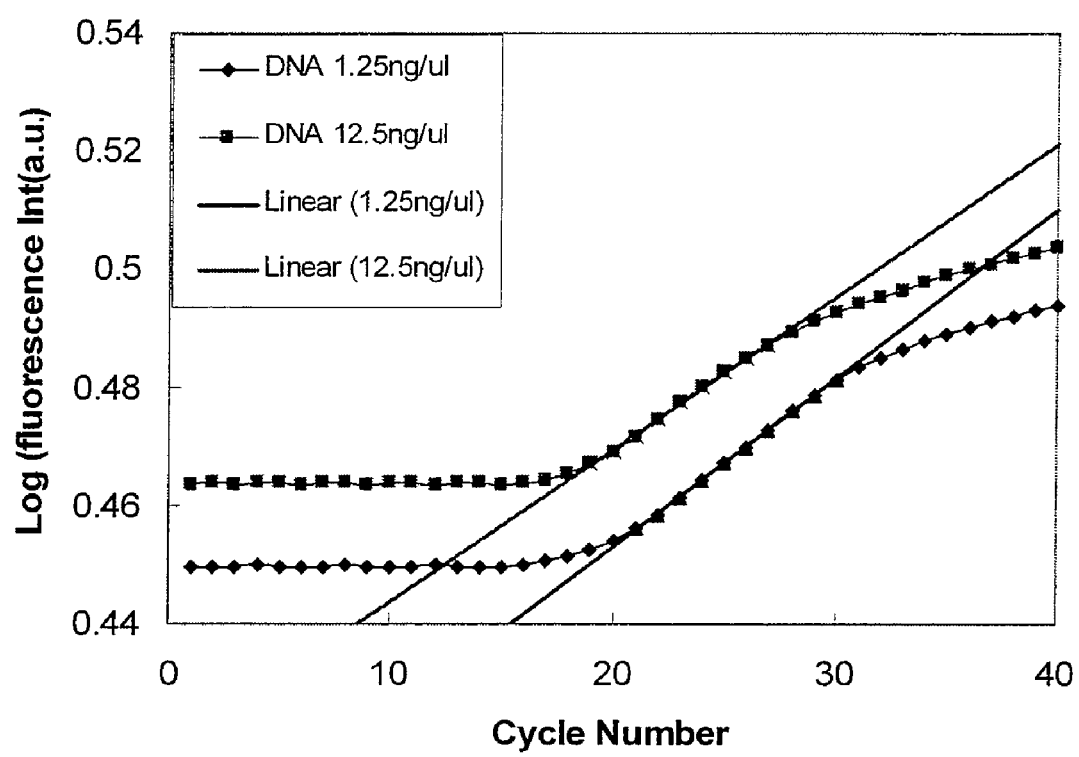
FIG. 15 is a graph of Fluorescence intensity curves obtained by fiber optical detection system from real-time PCR of 150 bp E. coli O157:H7 stx 1 DNA.

Using the newly developed laser-optic fiber detection system, real-time detection of 150 bp *E. coli* O157:H7 stx 1 gene in our PCR module can be accomplished. Some preliminary results are shown in FIG. 15. The fluorescence intensity curves show three phases representing the three characteristic phases of the PCR reaction, that is, the flat first phase, the exponential increase (the second) phase (linear line in Log scale in Y axis), and the saturation phase. FIG. 15 shows the results of two PCR runs with different initial DNA concentrations. For DNA concentrations 12.5 ng/µl and 1.25 ng/µl, the threshold cycle numbers (the starting point of the exponential increase phase) are 19 and 21, respectively. The fluorescence intensity curves are similar to those obtained using a commercial real-time PCR machine, indicating our miniaturized fluorescence detection system works well.

Accordingly, by the practice of the present invention, reaction modules, as well as methods, systems, and devices related to chemical reactions, notably PCR, having heretofore unrecognized characteristics are described.

The disclosures of all cited patents and publications referred to in this application are incorporated herein by reference.

The above description is intended to enable the person skilled in the art to practice the invention. It is not intended to detail all of the possible variations and modifications that will become apparent to the skilled worker upon reading the description. It is intended, however, that all such modifications and variations be included within the scope of the invention that is defined by the following claims. The claims are intended to cover the indicated elements and steps in any arrangement or sequence that is effective to meet the objectives intended for the invention, unless the context specifically indicates the contrary.

What is claimed is:

1. A miniature multiplex fluorescence detection system for detecting fluorescence emissions from at least one sample on a reactor module having a plurality of reaction wells, the system comprising:
   at least one light source coupled to the reaction wells, for generating light at excitation wavelengths;
   at least one detector for receiving detection wavelengths from the reaction wells; and
   an optical switching device, coupled between the detector and the reaction wells, to direct emissions of fluorescence to the detector.

2. The system of claim 1, further comprising a filter for directing light from at least one light source to the optical switching device and for directing the fluorescence emissions to at least one detector, wherein the light from the at least one light source is directed to the reaction wells by the optical switching device.

3. The system of claim 1 wherein at least one light source is a semiconductor laser.

4. The system of claim 1 wherein at least one detector is a PIN photo detector.

5. The system of claim 1, further comprising a heating and cooling module coupled to the reactor module for modulating a temperature of the sample.

6. The system of claim 1, further comprising a housing for hosting the light source, detector, switching device, heating and cooling module, and a stage for coupling to the reactor module, wherein a slot is provided in the housing for inserting the reactor module therein.

7. A device for real-time monitoring of a temperature-controlled chemical reaction involving fluorescence emission-detection, the device comprising:
   a multiplex fluorescence detection system for detecting fluorescence emissions from fluid samples contained in reaction wells, the system comprising:
      at least one light source coupled to the reaction wells, for generating light at excitation wavelengths;
      at least one detector for receiving detection wavelengths from the reaction wells; and
      an optical switching device, coupled between the detector and the reaction wells, to direct emissions of fluorescence to the detector;
   a heating and cooling module for modulating a temperature of the samples; and
   a control module for controlling the fluorescence detection system and monitoring the chemical reaction by processing the fluorescence emissions.

8. The device of claim 7, further comprising a disposable reactor module comprising a substrate and a layer of polymer on the substrate, with the layer of polymer having the reaction wells for receiving fluid samples.

9. The system of claim 8 wherein the polymer is poly (dimethylsiloxane) (PDMS).

10. The system of claim 8 wherein the layer of polymer has a plurality of grooves around the reaction wells.

11. The device of claim 7 further comprising a sealant for reducing evaporation of the fluid samples contained in the reaction wells out of the reaction wells.

12. The device of claim 7, further comprising a filter for directing light from at least one light source to the optical switching device and directing the fluorescence emissions to at least one detector, wherein the light from at least one light source is directed to the reaction wells by the optical switching device.

13. The device of claim 7, wherein at least one light source is a semiconductor laser.

14. The device of claim 7 wherein at least one detector is a PIN photo detector.

15. The device of claim 8 further comprising a housing for hosting the light source, detector, switching device, heating and cooling module, and stage, and wherein a slot is provided in the housing for inserting the reactor module therein.

16. The device of claim 7 wherein the control module is integrated within the fluorescence detection system.

17. The device of claim 7, wherein the device is portable.

18. The device of claim 7, wherein the chemical reaction is a Polymerase Chain Reaction (PCR).

* * * * *

UNITED STATES PATENT AND TRADEMARK OFFICE
CERTIFICATE OF CORRECTION

PATENT NO. : 7,795,014 B2  Page 1 of 1
APPLICATION NO. : 12/535526
DATED : September 14, 2010
INVENTOR(S) : Dongqing Li It is certified that error appears in the above-identified patent and that said Letters Patent is hereby corrected as shown below:

Col. 22, line 13, in claim 9, delete "The system" and insert -- The device --

Col. 22, line 15, in claim 10, delete "The system" and insert -- The device --

Signed and Sealed this
Thirty-first Day of January, 2012

David J. Kappos
*Director of the United States Patent and Trademark Office*